(12) United States Patent
Murai et al.

(10) Patent No.: US 8,680,268 B2
(45) Date of Patent: Mar. 25, 2014

(54) SULFONIC ACID DERIVATIVE COMPOUND AND NOVEL NAPHTHALIC ACID DERIVATIVE COMPOUND

(75) Inventors: Toshihiko Murai, Tokyo (JP); Yoshie Makabe, Tokyo (JP); Shohei Fujita, Tokyo (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 13/521,855

(22) PCT Filed: Jan. 12, 2011

(86) PCT No.: PCT/JP2011/050333
§ 371 (c)(1),
(2), (4) Date: Jul. 12, 2012

(87) PCT Pub. No.: WO2011/087011
PCT Pub. Date: Jul. 21, 2011

(65) Prior Publication Data
US 2012/0289697 A1    Nov. 15, 2012

(30) Foreign Application Priority Data

Jan. 13, 2010 (JP) ................................ 2010-005289

(51) Int. Cl.
*C07D 221/06* (2006.01)
*C07D 311/78* (2006.01)
*C07D 413/12* (2006.01)

(52) U.S. Cl.
USPC .............................. 544/126; 546/98; 549/232

(58) Field of Classification Search
None
See application file for complete search history.

(56) References Cited

U.S. PATENT DOCUMENTS

2005/0208425 A1    9/2005 Ogiso et al.

FOREIGN PATENT DOCUMENTS

| JP | 57-151651 A | 9/1982 |
| JP | 8-501890 A | 2/1996 |
| JP | 2004-217748 A | 8/2004 |
| JP | 2009-516207 A | 4/2009 |
| WO | WO 94/10608 A1 | 5/1994 |
| WO | WO 03/035407 A1 | 5/2003 |
| WO | WO 2007/054813 A2 | 5/2007 |

OTHER PUBLICATIONS

Peters et al., 36(7) J. Chem. Tech. & Biotech. 319-28 (1986).*
Da, Settimo A. et al.: "Synthesis and local anesthetic activity of some N-β-Diethylaminoethylnaphthalimides", Il Farmaco, Edizione Scientifica, vol. 37, No. 2, 1982, pp. 105-115.
PCT/ISA/210—International Search Report mailed on Apr. 5, 2011, issued in PCT/JP2011/050333.
Peters, Arnold T. et al.: "Thioethers and Sulphones of 7H-Benzimidazo(2,1-a)benz(d,e)isoquinolin-7-one: Dyes for Synthetic-polymer Fibres", Journal of Chemical Technology and Biotechnology, vol. 36, No. 7, 1986, pp. 319-328.
Steidl, L. et al.: "Non-ionic photoacid generators for applications in two-photon lithography", Journal of Materials Chemistry, vol. 19, No. 4, 2009, pp. 505-513.
Tao, Z. et al.: "Synthesis of Furonaphthalimides as Novel DNA intercalators", Dyes and Pigments, vol. 30, No. 4, 1996, pp. 247-252.

* cited by examiner

*Primary Examiner* — Janet L Andres
*Assistant Examiner* — Timothy R Rozof
(74) *Attorney, Agent, or Firm* — Birch, Stewart, Kolasch & Birch, LLP

(57) ABSTRACT

Disclosed are a novel sulfonic acid derivative compound and a novel naphthalic acid derivative compound with high solubility in organic solvents, good photosensitivity, and suitability as a photoacid generator and a polymerization initiator. The sulfonic acid derivative compound is represented by the formula (I)

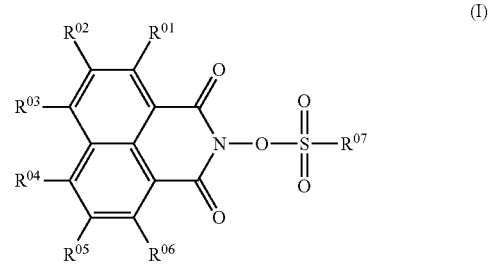

(wherein $R^{01}$, $R^{04}$, $R^{05}$, and $R^{06}$ represent a hydrogen atom; any one of $R^{02}$ and $R^{03}$ represents an alkoxy group having a carbon number of 4 to 18 which may be substituted with an alicyclic hydrocarbon group, a heterocyclic group, or a halogen atom and which may have a branch, or the like; and $R^{07}$ represents an aliphatic hydrocarbon group having a carbon number of 1 to 18 which may be substituted with a halogen atom and/or an alkylthio group, or the like).

7 Claims, No Drawings

SULFONIC ACID DERIVATIVE COMPOUND AND NOVEL NAPHTHALIC ACID DERIVATIVE COMPOUND

TECHNICAL FIELD

The present invention relates to novel sulfonic acid derivative compounds and particularly to a sulfonic acid derivative compound which is useful as a photoacid generator and a cationic polymerization initiator and gives absorption characteristics and solubility. The present invention also relates to a novel naphthalic acid derivative which gives the above described novel sulfonic acid derivative compound.

BACKGROUND ART

A sulfonyloxyimide having a naphthalimino group which is a radiation functional group is a substance that generates an acid by irradiation with an energy ray such as light and is used in a photoacid generator in a resist composition for photolithography, used for forming an electronic circuit such as a semiconductor; a cationic polymerization initiator in a resin composition for laser lithography or a photopolymerizable composition such as a paint, a coating, an adhesive, or an ink; or the like.

Patent Literature 1 discloses a curable composition comprising an acid-curable resin and a latent curing agent catalyst represented by the formula (II). It is disclosed that, in the formula (II), $R^1$ to $R^4$ which are substituents with naphthalene skeletons are a hydrogen atom, an alkyl group having a carbon number of 1 to 8, an alkoxy group having a carbon number of 1 to 4, an alkylthio group having 1 to 12 carbon atoms, a nitro group, or a halogen atom. Patent Literature 1 only discloses $R^1$ to $R^4$ which are hydrogen atoms but neither discloses nor suggests differences in properties and abilities depending on the kinds of the substitutions thereof, the number of the substitutions, the positions of the substitutions, and/or the like.

Patent Literature 2 discloses a photoresist comprising, as a sulfonic acid precursor, a sulfonyloxyimide represented by the formula (I), and used in an ultraviolet ray, electron beam or X-ray exposure device. Patent Literature 2 discloses naphthalimide, 3-nitronaphthalimide, 4-nitronaphthalimide, 4-chloronaphthalimide, and 4-bromonaphthalimide as naphthalimides.

Patent Literature 3 discloses an active beam-curable ink composition containing a sulfonic acid generator represented by the formula (A-1). An alkyl group, an alkoxy group, a carbonyl group, a phenylthio group, a halogen atom, a cyano group, a nitro group, and a hydroxy group are disclosed as $R_1$ and $R_2$ which are substituents with naphthalene skeletons in the formula (A-1).

Patent Literature 4 discloses a composition for an undercoat for a photoresist, discloses fluorinated sulfonyloxyimide having a naphthalimino group as a photoactive compound, and discloses ($C_1$-$C_8$) alkyl or ($C_1$-$C_8$) alkoxy as a substituent with a naphthalene skeleton. However, there is neither disclosure nor suggestion of differences in properties and abilities depending on the kinds of the substitutions, the positions of the substitutions, and/or the like.

Sulfonyloxyimides having naphthalimino groups according to the above described patent literatures have had compatibility with organic components such as organic solvents and resin components and photosensitivity in the long-wavelength side that have been poor as photoacid generators used in photoresists; and cationic polymerization initiators used in resin compositions for laser lithography, paints, coatings, adhesives, inks, and the like.

RELATED ART DOCUMENTS

Patent Documents

Patent Document 1: Japanese Unexamined Patent Application Publication No. S57-151651 (claim 1)

Patent Document 2: Japanese Unexamined Patent Application Publication (Translation of PCT Application) No. H8-501890 (claim 2)

Patent Document 3: Japanese Unexamined Patent Application Publication No. 2004-217748 (claim 1)

Patent Document 4: Japanese Unexamined Patent Application Publication (Translation of PCT Application) No. 2009-516207 (paragraphs [0029] and [0034])

SUMMARY OF THE INVENTION

Problems to be Solved by the Invention

Accordingly, an object of the present invention is to provide a novel sulfonic acid derivative compound and a novel naphthalic acid derivative compound with high solubility in organic solvents, good photosensitivity, and suitability as a photoacid generator and a polymerization initiator.

Solution to Problem

As a result of extensive research for solving the above described problem, the present inventors found that a sulfonic acid derivative compound comprising a naphthalimino group having a specific structure as an ester component has good solubility and good photosensitivity and arrived at the present invention.

Specifically, the sulfonic acid derivative compound according to the present invention is represented by the formula (I)

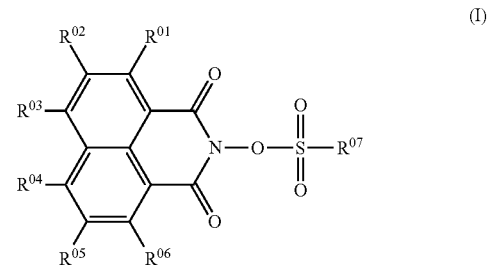

(wherein $R^{01}$, $R^{04}$, $R^{05}$, and $R^{06}$ represent a hydrogen atom; any one of $R^{02}$ and $R^{03}$ represents an alkoxy group having a carbon number of 4 to 18 which may be substituted with an alicyclic hydrocarbon group, a heterocyclic group, or a halogen atom and which may have a branch; a group in which a methylene group which is not adjacent to an oxygen atom in the alkoxy group but is at an optional position is substituted with —C(=O)— group; a group in which the alkoxy group is interrupted by a —O—C(=O)— bond or a —OC(=O)—NH— bond from closer proximity to a naphthalene ring; an alkylthio group having a carbon number of 4 to 18 which may be substituted with an alicyclic hydrocarbon group, a heterocyclic group, or a halogen atom and which may have a branch;

a group in which a methylene group which is not adjacent to a sulfur atom in the alkylthio group but is at an optional position is substituted with a —C(=O)— group; a group in which the alkylthio group is interrupted by a —O—C(=O)— bond or a —OC(=O)—NH— bond from closer proximity to a naphthalene ring; or a group represented by the formula (A) as described below; the remaining one of $R^{02}$ and $R^{03}$ represents a hydrogen atom; and $R^{07}$ represents an aliphatic hydrocarbon group having a carbon number of 1 to 18 which may be substituted with a halogen atom and/or an alkylthio group; an alkyl group having a carbon number of 1 to 18 which may be substituted with a halogen atom and/or an alicyclic hydrocarbon group and which may have a branch; an alicyclic hydrocarbon group having a carbon number of 3 to 18 which may be substituted with a halogen atom; an awl group having a carbon number of 6 to 20 which may be substituted with a halogen atom and/or an alkylthio group having a carbon number of 1 to 18; an arylalkyl group having a carbon number of 7 to 20 which may be substituted with a halogen atom and/or an alkylthio group having a carbon number of 1 to 18; an alkylaryl group having a carbon number of 7 to 20 which may be substituted with a halogen atom; an aryl group having a carbon number of 7 to 20 which is substituted with an acyl group; 10-camphoryl; or a group represented by the formula (B) as described below)

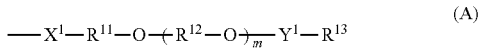

(wherein $X^1$ represents an oxygen atom or a sulfur atom; $Y^1$ represents a single bond or an alkanediyl group having a carbon number of 1 to 4; $R^{11}$ represents a hydrocarbon group having a carbon number of 1 to 12; $R^{12}$ represents an alkanediyl group having a carbon number of 1 to 4; $R^{13}$ represents a hydrogen atom, an alkyl group having a carbon number of 1 to 4 which may have a branch, or an alicyclic hydrocarbon group or a heterocyclic group having a carbon number of 3 to 10; m represents 0 to 5; and plural $R^{12}$ may be the same or different when m is 2 to 5)

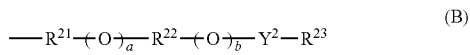

(wherein $Y^2$ represents a single bond or an alkanediyl group having a carbon number of 1 to 4; $R^{21}$ represents an alkanediyl group having a carbon number of 2 to 6, a halogenated alkanediyl group having a carbon number of 2 to 6, an arylene group having a carbon number of 6 to 20, or a halogenated arylene group having a carbon number of 6 to 20; $R^{22}$ represents a single bond, an alkanediyl group having a carbon number of 2 to 6, a halogenated alkanediyl group having a carbon number of 2 to 6, an arylene group having a carbon number of 6 to 20, or a halogenated arylene group having a carbon number of 6 to 20; $R^{23}$ represents an alkyl group having a carbon number of 1 to 18 which may have a branch, a halogenated alkyl group having a carbon number of 1 to 18 which may have a branch, an alicyclic hydrocarbon group having a carbon number of 3 to 12, an aryl group having a carbon number of 6 to 20, a halogenated aryl group having a carbon number of 6 to 20, an arylalkyl group having a carbon number of 7 to 20, or a halogenated arylalkyl group having a carbon number of 7 to 20; a and b represent 0 or 1; and either a or b is 1).

In the sulfonic acid derivative compound according to the present invention, the $R^{07}$ is preferably a perfluoroalkyl group having a carbon number of 1 to 8.

Further, in the sulfonic acid derivative compound according to the present invention, the $R^{07}$ is preferably 10-camphoryl.

Further, the compound according to the present invention is represented by the formula (II) as described below

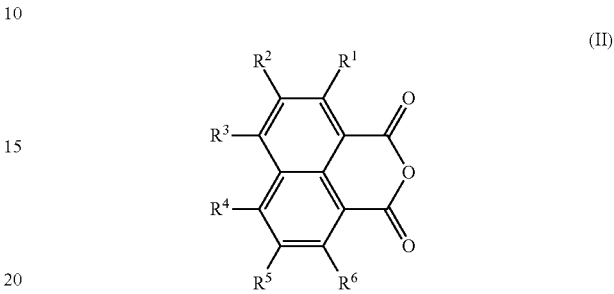

(wherein $R^1$, $R^4$, $R^5$, and $R^6$ represent a hydrogen atom; any one of $R^2$ and $R^3$ represents an alkylthio group having a carbon number of 4 to 18 which may be substituted with an alicyclic hydrocarbon group, a heterocyclic group, or a halogen atom and which may have a branch; a group in which a methylene group which is not adjacent to a sulfur atom in the alkylthio group but is at an optional position is substituted with a —C(=O)— group; a group in which the alkylthio group is substituted with a —O—C(=O)— bond or a —OC(=O)—NH— bond from closer proximity to a naphthalene ring; or a group represented by the formula (C) as described below; and the remaining one of $R^2$ and $R^3$ represents a hydrogen atom)

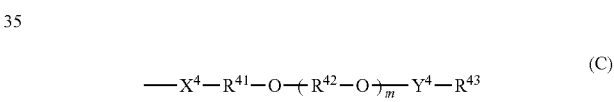

(wherein $X^4$ represents an oxygen atom or a sulfur atom; $Y^4$ represents a single bond or an alkanediyl group having a carbon number of 1 to 4; $R^{41}$ represents a hydrocarbon group having a carbon number of 1 to 12; $R^{42}$ represents an alkanediyl group having a carbon number of 1 to 4; $R^{43}$ represents an alkyl group having a carbon number of 1 to 4 which may have a branch or an alicyclic hydrocarbon group or a heterocyclic group having a carbon number of 3 to 10; m represents 0 to 5; and plural $R^{42}$ may be the same or different when m is 2 to 5).

Further, the compound according to the present invention is represented by the formula (III) as described below

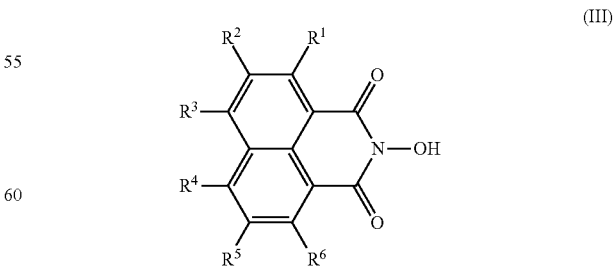

(wherein $R^1$, $R^4$, $R^5$, and $R^6$ represent a hydrogen atom; any one of $R^2$ and $R^3$ represents an alkylthio group having a carbon number of 4 to 18 which may be substituted with an alicyclic hydrocarbon group, a heterocyclic group, or a halogen atom and which may have a branch; a group in which a methylene group which is not adjacent to a sulfur atom in the alkylthio group but is at an optional position is substituted with a —C(=O)— group; a group in which the alkylthio group is substituted with a —O—C(=O)— bond or a —OC(=O)—NH— bond from closer proximity to a naphthalene ring; or a group represented by the formula (D) as described below; and the remaining one of R² and R³ represents a hydrogen atom)

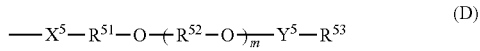
(D)

(wherein $X^5$ represents an oxygen atom or a sulfur atom; $Y^5$ represents a single bond or an alkanediyl group having a carbon number of 1 to 4; $R^{51}$ represents a hydrocarbon group having a carbon number of 1 to 12; $R^{52}$ represents an alkanediyl group having a carbon number of 1 to 4; $R^{53}$ represents an alkyl group having a carbon number of 1 to 4 which may have a branch or a hydrocarbon group or a heterocyclic group having a carbon number of 3 to 10; m represents 0 to 5; and plural $R^{52}$ may be the same or different when m is 2 to 5).

Advantageous Effects of Invention

In accordance with the present invention, there can be provided a novel sulfonic acid derivative compound with good solubility in organic solvents and good photosensitivity in the long-wavelength side which are useful abilities as a photoacid generator and a cationic polymerization initiator. Further, in accordance with the present invention, there can be provided a naphthalic acid derivative which is an intermediate that imparts the above described novel sulfonic acid derivative compound with particularly good properties.

DESCRIPTION OF EMBODIMENT

The compounds according to the present invention will be described in detail below.

The sulfonic acid derivative compound according to the present invention is a novel compound represented by the formula (I). A feature of the sulfonic acid derivative compound according to the present invention is that $R^{02}$ and $R^{03}$ which are the substituents of a naphthalimino group have specific organic groups through an oxygen atom or a sulfur atom. The useful characteristic of the sulfonic acid derivative compound according to the present invention is obtained by the effect of the specific organic group.

In the alkoxy group and the alkylthio group having a carbon number of 4 to 18 which are represented by $R^{02}$ or $R^{03}$ in the above described formula (I), may be substituted with an alicyclic hydrocarbon group, a heterocyclic group, or a halogen atom, and may have a branch, the total carbon number of the alicyclic hydrocarbon group and the heterocyclic group is 4 to 18. Since a carbon number of less than 4 causes poor solubility and a carbon number of more than 18 causes deterioration in photosensitivity and acid generation ability per molecule, any effect expected sufficiently for a used amount cannot be produced. Further, the alicyclic hydrocarbon group and the heterocyclic group may also be present in the form of being substituted with a methylene group in an alkoxy or alkylthio group, may also be present in the form of being substituted with a proton in a methylene group in an alkoxy group or an alkylthio group, or may also be present in a terminal in an alkoxy or alkylthio group. Further, the alkoxy group and the alkylthio group also comprise a group constituted by directly binding oxygen atoms or sulfur atoms to carbon atoms that constitute the ring structure of the alicyclic hydrocarbon group or the heterocyclic group. Further, halogen atoms include fluorine, chlorine, bromine, and iodine.

Among alkoxy groups as described above, those having neither alicyclic hydrocarbon groups nor heterocyclic groups include butyloxy, sec-butyloxy, tert-butyloxy, isobutyloxy, amyloxy, isoamyloxy, tert-amyloxy, hexyloxy, heptyloxy, isoheptyloxy, tert-heptyloxy, octyloxy, isooctyloxy, tert-octyloxy, 2-ethylhexyloxy, nonyloxy, decyloxy, undecyloxy, dodecyloxy, tridecyloxy, tetradecyloxy, pentadecyloxy, hexadecyloxy, heptadecyloxy, and octadecyloxy.

Among alkylthio groups as described above, those having neither alicyclic hydrocarbon groups nor heterocyclic groups include butylthio, sec-butylthio, tert-butylthio, isobutylthio, amylthio, isoamylthio, tert-amylthio, hexylthio, heptylthio, isoheptylthio, tert-heptylthio, octylthio, isooctylthio, tert-octylthio, 2-ethylhexylthio, nonylthio, decylthio, undecylthio, dodecylthio, tridecylthio, tetradecylthio, pentadecylthio, hexadecylthio, heptadecylthio, and octadecylthio.

Examples of alicyclic hydrocarbon groups present in the above described alkoxy groups or alkylthio groups, based on the names of cycloalkanes constituting the alicyclic hydrocarbon groups, include cyclopropane, cyclobutane, cyclopentane, cyclohexane, cycloheptane, cyclooctane, cyclodecane, bicyclo[2.1.1]hexane, bicyclo[2.2.1]heptane, bicyclo[3.2.1]octane, bicyclo[2.2.2]octane, and adamantane.

In examples of heterocyclic groups present in the above described alkoxy groups or alkylthio groups, based on the names of heterocycles constituting the heterocyclic groups, examples of heterocycles having a carbon number of 3 to 10, based on the names of heterocycles constituting the heterocycles, include pyrrole, thiophene, furan, pyran, thiopyran, imidazole, pyrazole, thiazole, isothiazole, oxazole, isoxazole, pyridine, pyrazine, pyrimidine, pyridazine, pyrrolidine, pyrazolidine, imidazolidine, isooxazolidine, isothiazolidine, piperidine, piperazine, morpholine, thiomorpholine, chroman, thiochroman, isochroman, isothiochroman, indoline, isoindoline, pyrindine, indolizine, indole, indazole, purine, quinolizine, isoquinoline, quinoline, naphthyridine, phthalazine, quinoxaline, quinazoline, cinnoline, pteridine, acridine, perimidine, phenanthroline, carbazole, carboline, phenazine, anthyridine, thiadiazole, oxadiazole, triazine, triazole, tetrazole, benzimidazole, benzoxazole, benzothiazole, benzothiadiazole, benzofuroxan, naphthoimidazole, benzotriazole, tetraazaindene, and saturated heterocycles (such as a tetrahydrofuran ring) hydrogenated with unsaturated bonds or conjugated bonds present in the above described heterocycles.

Among the above described alkoxy groups, specific examples of those having alicyclic hydrocarbon groups include cyclopentyloxy, methylcyclopentyloxy, cyclohexyloxy, fluorocyclohexyloxy, chlorocyclohexyloxy, cyclohexylmethyloxy, methylcyclohexyloxy, norbornyloxy, ethylcyclohexyloxy, cyclohexylethyloxy, dimethylcyclohexyloxy, methylcyclohexylmethyloxy, norbornylmethyloxy, trimethylcyclohexyloxy, 1-cyclohexylbutyloxy, adamanthyloxy, menthyloxy, n-butylcyclohexyloxy, tert-butylcyclohexyloxy, bornyloxy, isobornyloxy, decahydronaphthyloxy, dicyclopentadienoxy, 1-cyclohexylpentyloxy, methyladamanthyloxy, adamantanemethyloxy, 4-amylcyclohexyloxy, cyclohexylcyclohexyloxy, adamanthylethyloxy, dimethyladamanthyloxy, and the like; among the above described alkoxy groups, specific examples of those having heterocyclic groups include tetrahydrofuranyloxy, furfuryloxy, tetrahydrofurfuryloxy, tetrahydropyranyloxy, butyrolactyloxy, butyrolactylmethyloxy, and indoleoxy; among the above described alkylthio groups, specific examples of those having alicyclic hydrocarbon groups include cyclopentylthio, cyclohexylthio, cyclohexylmethylthio, norbornylthio, iso-norbornylthio, and the like; and, among the above described alkylthio groups, specific examples of those having heterocyclic groups include furfurylthio and tetrahydrofurfurylthio.

Groups in which methylene which is not adjacent to an oxygen atom in the above described alkoxy group having a carbon number of 4 to 18 is substituted with a —C(=O)— group include 2-ketobutyl-1-oxy, 2-ketopentyl-1-oxy, 2-ketohexyl-1-oxy, 2-ketoheptyl-1-oxy, 2-ketooctyl-1-oxy, 3-ketobutyl-1-oxy, 4-ketoamyl-1-oxy, 5-ketohexyl-1-oxy, 6-ketoheptyl-1-oxy, 7-ketooctyl-1-oxy, 3-methyl-2-ketopentane-4-oxy, 2-keto-pentane-4-oxy, 2-methyl-2-ketopentane-4-oxy, 3-ketoheptane-5-oxy, and 2-adamantanone-5-oxy.

Groups in which methylene which is not adjacent to an sulfur atom in the above described alkylthio group having a carbon number of 4 to 18 is substituted with a —C(=O)— group include 2-ketobutyl-1-thio, 2-ketopentyl-1-thio, 2-ketohexyl-1-thio, 2-ketoheptyl-1-thio, 2-ketooctyl-1-thio, 3-ketobutyl-1-thio, 4-ketoamyl-1-thio, 5-ketohexyl-1-thio, 6-ketoheptyl-1-thio, 7-ketooctyl-1-thio, 3-methyl-2-ketopentane-4-thio, 2-keto-pentane-4-thio, 2-methyl-2-ketopentane-4-thio, 3-ketoheptane-5-thio, and the like.

Further, the group in which the alkoxy group having a carbon number of 4 to 18 is interrupted by a —O—C(=O)— bond or a —OC(=O)—NH— bond from closer proximity to a naphthalene ring and the group in which the alkylthio group having a carbon number of 4 to 18 is interrupted by a —O—C(=O)— bond or a —OC(=O)—NH— bond from closer proximity to a naphthalene ring are —X—R—O—C(=O)—R' and —X—R—OC(=O)—NH—R', wherein X is an oxygen atom or a sulfur atom; and R and R' are groups which can form $R^{02}$ and $R^{03}$ defined in the formula (I), respectively, that is, R is an alkylene group which may be substituted with an alicyclic hydrocarbon group, a heterocyclic group, or a halogen atom and which may have a branch, R' is an alkyl group which may be substituted with an alicyclic hydrocarbon group, a heterocyclic group, or a halogen atom and which may have a branch, and the total carbon number of R and R' is 4 to 18.

In the above described formula (A), such hydrocarbon groups having a carbon number of 1 to 12 represented by $R^{11}$ include aliphatic hydrocarbon groups such as alkanediyl groups, alkenediyl groups, and alkyndiyl groups, alicyclic hydrocarbon groups such as cycloalkanediyl groups, and groups in which alicyclic hydrocarbon and aliphatic hydrocarbon are bound. For example, mention is made of methylene, ethylene, propane-1,3-diyl, propane-1,2-diyl, butylene, butane-1,3-diyl, butane-2,3-diyl, butane-1,2-diyl, pentylene, hexylene, cyclohexylene, cyclohexylenemethyl, heptylene, octylene, cyclohexyleneethyl, methylenecyclohexylenemethyl, nonylene, decylene, adamantylene, norbornylene, iso-norbornylene, dodecylene, and undecylene.

In the above described formula (A), such alkanediyl groups having a carbon number of 1 to 4 represented by $Y^1$ and $R^{12}$ include methylene, ethylene, propane-1,3-diyl, propane-1,2-diyl, butylene, butane-1,3-diyl, butane-2,3-diyl, and butane-1,2-diyl.

In the above described formula (A), such alkyl groups having a carbon number of 1 to 4 which are represented by $R^{13}$ and may have a branch include methyl, ethyl, propyl, isopropyl, butyl, sec-butyl, tert-butyl, and isobutyl; examples of alicyclic hydrocarbon groups having a carbon number of 3 to 10, based on the names of cycloalkanes constituting the alicyclic hydrocarbon groups include cyclopropane, cyclobutane, cyclopentane, cyclohexane, cycloheptane, cyclooctane, cyclodecane, bicyclo[2.1.1]hexane, bicyclo[2.2.1]heptane, bicyclo[3.2.1]octane, bicyclo[2.2.2]octane, and adamantane; examples of heterocycles having a carbon number of 3 to 10, based on the names of heterocycles constituting the heterocycles, include pyrrole, thiophene, furan, pyran, thiopyran, imidazole, pyrazole, thiazole, isothiazole, oxazole, isoxazole, pyridine, pyrazine, pyrimidine, pyridazine, pyrrolidine, pyrazolidine, imidazolidine, isooxazolidine, isothiazolidine, piperidine, piperazine, morpholine, thiomorpholine, chroman, thiochroman, isochroman, isothiochroman, indoline, isoindoline, pyrindine, indolizine, indole, indazole, purine, quinolizine, isoquinoline, quinoline, naphthyridine, phthalazine, quinoxaline, quinazoline, cinnoline, pteridine, acridine, perimidine, phenanthroline, carbazole, carboline, phenazine, anthyridine, thiadiazole, oxadiazole, triazine, triazole, tetrazole, benzimidazole, benzoxazole, benzothiazole, benzothiadiazole, benzofuroxan, naphthoimidazole, benzotriazole, tetraazaindene, and saturated heterocycles (such as a tetrahydrofuran ring) hydrogenated with unsaturated bonds or conjugated bonds present in the above described heterocycles.

The sulfonic acid derivative compound according to the present invention, wherein $R^{02}$ or $R^{03}$ is an alkylthio group having a carbon number of 4 to 18 which may have an alicyclic hydrocarbon group or a heterocyclic group; a group in which a methylene group which is not adjacent to a sulfur atom in the alkylthio group having a carbon number of 4 to 18 but is at an optional position is substituted with a —C(=O)— group; and a group in which the alkylthio group having a carbon number of 4 to 18 is interrupted by a —O—C(=O)— bond or a —OC(=O)—NH— bond from closer proximity to a naphthalene ring, is preferred because of easy synthesis, and, especially, an alkylthio group having a carbon number of 6 to 18 is more preferable in terms of solubility and a production cost. Further, one wherein $R^{02}$ or $R^{03}$ is represented by the above described formula (A) is preferred since particularly solubility in organic agents such as organic solvents and photosensitive resins is good, and sensitivity is improved by increasing a blending amount and the preservation stability of a photosensitive material composition such as a photoresist or an adhesive is improved when it is used as a photoacid generator or a cationic polymerization initiator. In the above described formula (A), one wherein the total number of carbon atoms, oxygen atoms, and sulfur atoms is 4 to 18 is more preferable since solubility and photosensitivity are good, and one wherein $X^1$ is a sulfur atom is further preferable.

Furthermore, among the groups represented by the above described formula (A), groups, wherein $R^{11}$ is an alkanediyl group having a carbon number of 2 to 4; $R^{12}$ is an alkanediyl group having a carbon number of 1 to 4; $R^{13}$ is a hydrogen atom or an alkyl group having a carbon number of 1 to 4 which may have a branch; and m is 0 to 3, are preferred.

In the above described formula (I), in the aliphatic hydrocarbon group having a carbon number of 1 to 18 which may be substituted with a halogen atom and/or an alkylthio group having a carbon number of 1 to 18, the aryl group having a carbon number of 6 to 20 which may be substituted with a halogen atom and/or an alkylthio group having a carbon number of 1 to 18, the arylalkyl group having a carbon number of 7 to 20 which may be substituted with a halogen atom and/or an alkylthio group having a carbon number of 1 to 18, and the alkylaryl group having a carbon number of 7 to 20 which may be substituted with a halogen atom, represented by $R^{07}$, the halogen atoms which are substituents include chlorine, bromine, iodine, and fluorine, and the alkylthio groups having a carbon number of 1 to 18 include methylthio, ethylthio, propylthio, isopropylthio, butylthio, sec-butylthio, tert-butylthio, isobutylthio, amylthio, isoamylthio, tert-amylthio, hexylthio, heptylthio, isoheptylthio, tert-heptylthio, octylthio, isooctylthio, tert-octylthio, 2-ethylhexylthio, nonylthio, decylthio, undecylthio, dodecylthio, tridecylthio, tetradecylthio, pentadecylthio, hexadecylthio, heptadecylthio, and octadecylthio.

In the above described formula (I), in the aliphatic hydrocarbon group having a carbon number of 1 to 18 which is represented by $R^{07}$ and may be substituted with a halogen atom and/or an alkylthio group, the aliphatic hydrocarbon group having a carbon number of 1 to 18 includes an alkenyl group, an alkyl group, an alicyclic hydrocarbon group, a group in which a methylene group in an alkyl group is substituted with an alicyclic hydrocarbon group, a group in which a proton in a methylene group in an alkyl group is substituted with an alicyclic hydrocarbon group, or a group in which an alicyclic hydrocarbon is present in a terminal in an alkyl group. The alkenyl group includes allyl or 2-methyl-2-propenyl; the alkyl group includes methyl, ethyl, propyl, isopropyl, butyl, sec-butyl, tert-butyl, isobutyl, amyl, isoamyl, tert-amyl, hexyl, 2-hexyl, 3-hexyl, heptyl, 2-heptyl, 3-heptyl, isoheptyl, tert-heptyl, octyl, isooctyl, tert-octyl, 2-ethylhexyl, nonyl, isononyl, decyl, dodecyl, tridecyl, tetradecyl, pentadecyl, hexadecyl, heptadecyl, or octadecyl; and examples of the alicyclic hydrocarbon group, based on the names of cycloalkanes constituting the alicyclic hydrocarbon group, include cyclopropane, cyclobutane, cyclopentane, cyclohexane, cycloheptane, cyclooctane, cyclodecane, bicyclo[2.1.1]hexane, bicyclo[2.2.1]heptane, bicyclo[3.2.1]octane, bicyclo[2.2.2]octane, and adamantane.

Such aliphatic hydrocarbon groups having a carbon number of 1 to 18 substituted with a halogen atom as described above include, for example, halogenated alkyl groups such as trifluoromethyl, pentafluoroethyl, 2-chloroethyl, 2-bromoethyl, heptafluoropropyl, 3-bromopropyl, nonafluorobutyl, tridecafluorohexyl, heptadecafluorooctyl, 2,2,2-trifluoroethyl, 1,1-difluoroethyl, 1,1-difluoropropyl, 1,1,2,2-tetrafluoropropyl, 3,3,3-trifluoropropyl, 2,2,3,3,3-pentafluoropropyl, norbornyl-1,1-difluoroethyl, norbornyltetrafluoroethyl, and adamantane-1,1,2,2-tetrafluoropropyl; aliphatic hydrocarbons having a carbon number of 1 to 18 substituted with an alkylthio group include 2-methylthioethyl, 4-methylthiobutyl, 4-butylthioethyl, and the like; and aliphatic hydrocarbon groups having a carbon number of 1 to 18 substituted with a halogen atom and an alkylthio group having a carbon number of 1 to 18 include 1,1,2,2-tetrafluoro-3-methylthiopropyl and the like.

Such alicyclic hydrocarbon groups having a carbon number of 3 to 18 which are represented by $R^{07}$ in the above described formula (I) and may be substituted with a halogen atom include the same as described above.

In the above described formula (I), in the aryl group having a carbon number of 6 to 20 which is represented by $R^{07}$ and may be substituted with a halogen atom and/or an alkylthio group having a carbon number of 1 to 18, the aryl group includes phenyl, naphthyl, 4-vinylphenyl, biphenyl, or the like.

The above described aryl group having a carbon number of 6 to 20 substituted with a halogen atom includes pentafluorophenyl, chlorophenyl, dichlorophenyl, trichlorophenyl, 2,4-bis(trifluoromethyl)phenyl, bromoethylphenyl, or the like; the aryl group having a carbon number of 6 to 20 substituted with an alkylthio group having a carbon number of 1 to 18 includes 4-methylthiophenyl, 4-butylthiophenyl, 4-octylthiophenyl, or 4-dodecylthiophenyl; and the aryl group having a carbon number of 6 to 20 substituted with a halogen atom and an alkylthio group having a carbon number of 1 to 18 includes 1,2,5,6-tetrafluoro-4-methylthiophenyl, 1,2,5,6-tetrafluoro-4-butylthiophenyl, 1,2,5,6-tetrafluoro-4-dodecylthiophenyl, or the like.

In the above described formula (I), the carbon number of the aryl group having a carbon number of 7 to 20 which is represented by $R^{07}$ and substituted with an acyl group is one in which an acyl group is included. For example, mention is made of acetylphenyl, acetylnaphthyl, benzoylphenyl, 1-anthraquinolyl, and 2-anthraquinolyl.

In the above described formula (I), in the arylalkyl group having a carbon number of 7 to 20 which is represented by $R^{07}$ and may be substituted with a halogen atom and/or an alkylthio group having a carbon number of 1 to 18, the arylalkyl group having a carbon number of 7 to 20 includes benzyl, phenethyl, 2-phenylpropane-2-yl, diphenylmethyl, triphenylmethyl, styryl, cinnamyl, or the like.

The above described arylalkyl group substituted with a halogen atom includes, for example, pentafluorophenylmethyl, phenyldifluoromethyl, 2-phenyl-tetrafluoroethyl, 2-(pentafluorophenyl)ethyl, or the like; the arylalkyl group having a carbon number of 7 to 20 substituted with an alkylthio group having a carbon number of 1 to 18 includes p-methylthiobenzyl or the like; and the arylalkyl group substituted with a halogen atom and an alkylthio group having a carbon number of 1 to 18 includes 2,3,5,6-tetrafluoro-4-methylthiophenylethyl or the like.

In the above described formula (I), in the alkylaryl group having a carbon number of 7 to 20 which is represented by $R^{07}$ and may be substituted with a halogen atom, the alkylaryl group having a carbon number of 7 to 20 includes 2-methylphenyl, 3-methylphenyl, 4-methylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amyl phenyl, 2,5-di-tert-octylphenyl, cyclohexylphenyl, 2,4,5-trimethylphenyl, 2,4,6-trimethylphenyl, 2,4,6-triisopropylphenyl, or the like.

The above described formula (B) is an ether group. In the formula (B), such alkanediyl groups having a carbon number of 1 to 4 represented by $Y^2$ include methylene, ethylene, propane-1,3-diyl, propane-1,2-diyl, butylene, butane-1,3-diyl, butane-2,3-diyl, and butane-1,2-diyl; and such alkanediyl groups having a carbon number of 2 to 6 represented by $R^{21}$ or $R^{22}$ include ethylene, propane-1,3-diyl, propane-1,2-diyl, butylene, butane-1,3-diyl, butane-2,3-diyl, butane-1,2-diyl, pentane-1,5-diyl, pentane-1,3-diyl, pentane-1,4-diyl, pentane-2,3-diyl, hexane-1,6-diyl, hexane-1,2-diyl, hexane-1,3-diyl, hexane-1,4-diyl, hexane-2,5-diyl, hexane-2,4-diyl, hexane-3,4-diyl, and the like.

In the formula (B), the halogenated alkanediyl group having a carbon number of 2 to 6 represented by $R^{21}$ or $R^{22}$ is one at least one proton in the above described alkanediyl group having a carbon number of 2 to 6 is substituted with a halogen atom. Such halogen atoms include chlorine, bromine, iodine, and fluorine. For example, mention is made of tetrafluoroethylene, 1,1-difluoroethylene, 1-fluoroethylene, 1,2-difluoroethylene, hexafluoropropane-1,3-diyl, 1,1,2,2-tetrafluoropropane-1,3-diyl, 1,1,2,2-tetrafluoropentane-1,5-diyl, and the like.

In the formula (B), such arylene groups having a carbon number of 6 to 20 represented by $R^{21}$ or $R^{22}$ include 1,2-phenylene, 1,3-phenylene, 1,4-phenylene, 2,5-dimethyl-1,4-phenylene, 4,4'-biphenylene, diphenylmethane-4,4'-diyl, 2,2-diphenylpropane-4,4'-diyl, naphthalene-1,2-diyl, naphthalene-1,3-diyl, naphthalene-1,4-diyl, naphthalene-1,5- diyl, naphthalene-1,6-diyl, naphthalene-1,7-diyl, naphthalene-1,8-diyl, naphthalene-2,3-diyl, naphthalene-2,6-diyl, naphthalene-2,7-diyl, and the like.

In the formula (B), the halogenated arylene group having a carbon number of 6 to 20 represented by $R^{21}$ or $R^{22}$ is one in which at least one proton in the above described arylene group having a carbon number of 6 to 20 is substituted with a halogen atom. Such halogen atoms include chlorine, bromine, iodine, and fluorine. For example, mention is made of tetrafluorophenylene.

In the formula (B), such alkyl groups having a carbon number of 1 to 18 which are represented by $R^{23}$ and may have a branch include methyl, ethyl, propyl, isopropyl, butyl, sec-butyl, tert-butyl, isobutyl, amyl, isoamyl, tert-amyl, hexyl, 2-hexyl, 3-hexyl, heptyl, 2-heptyl, 3-heptyl, isoheptyl, tert-heptyl, octyl, isooctyl, tert-octyl, 2-ethylhexyl, nonyl, isononyl, decyl, dodecyl, tridecyl, tetradecyl, pentadecyl, hexadecyl, heptadecyl, and octadecyl.

In the formula (B), the halogenated alkyl group having a carbon number of 1 to 18 which is represented by $R^{23}$ and may have a branch is one in which at least one proton in the above described alkyl group having a carbon number of 1 to 18 is substituted with a halogen atom. Such halogen atoms include chlorine, bromine, iodine, and fluorine. For example, mention is made of halogenated alkyl groups such as trifluoromethyl, pentafluoroethyl, heptafluoropropyl, nonafluorobutyl, tridecafluorohexyl, heptadecafluorooctyl, 2,2,2-trifluoroethyl, 1,1-difluoroethyl, 1,1-difluoropropyl, 1,1,2,2-tetrafluoropropyl, 3,3,3-trifluoropropyl, 2,2,3,3,3-pentafluoropropyl, and 1,1,2,2-tetrafluorotetradecyl.

In the formula (B), examples of such alicyclic hydrocarbon groups having a carbon number of 3 to 12 represented by $R^{23}$, based on the names of cycloalkanes constituting the alicyclic hydrocarbon groups, include cyclopropane, cyclobutane, cyclopentane, cyclohexane, cycloheptane, cyclooctane, cyclodecane, bicyclo[2.1.1]hexane, bicyclo[2.2.1]heptane, bicyclo[3.2.1]octane, bicyclo[2.2.2]octane, and adamantane.

In the formula (B), such aryl groups having a carbon number of 6 to 20, such halogenated aryl groups having a carbon number of 6 to 20, such arylalkyl groups having a carbon number of 7 to 20, or such halogenated arylalkyl groups having a carbon number 7 to 20 represented by $R^{23}$ include the groups of which the examples are mentioned as $R^{07}$ described above.

Groups preferred as the formula (B) are groups in which fluorine is bound to a carbon atom adjacent to a sulfur atom in a group represented by $R^{21}$ and having a total carbon number of 2 to 18 because of having good acid generation and cationically polymerizable abilities.

As $R^{07}$ described above, a perfluoroalkyl group having a carbon number of 1 to 8 is preferred since the strength of a generated acid is high and high sensitivity is given, and 10-camphoryl which precludes diffusion of a generated acid and enables formation of a high-resolution resist pattern is preferred. The formula described below represents 10-camphoryl.

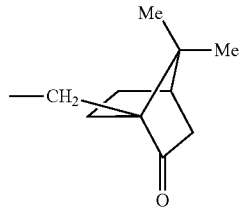

The naphthalic acid derivative compound according to the present invention is a novel compound represented by the formula (II) or (III). The naphthalic acid derivative compound gives a photosensitive group with characteristics useful particularly for the sulfonic acid derivative compound, as an intermediate for the sulfonic acid derivative compound according to the present invention as described above. The naphthalic acid derivative compound represented by the formula (III) is useful as a precursor for the sulfonic acid derivative compound represented by the formula (I) according to the present invention as described above; and the naphthalic acid derivative compound represented by the formula (II) according to the present invention is useful as a precursor for the naphthalic acid derivative compound represented by the formula (III) according to the present invention. A feature of these naphthalic acid derivative compounds is that $R^2$ and $R^3$ which are the substituents of a naphthalimino group have specific organic groups through an oxygen atom or a sulfur atom.

In the alkylthio group which is represented by $R^2$ or $R^3$ in the above described formula (II) or (III) and may be substituted with an alicyclic hydrocarbon group, a heterocyclic group, or a halogen atom, the total carbon number of the alicyclic hydrocarbon group and the heterocyclic group is 4 to 18. Since a carbon number of less than 4 causes poor solubility and a carbon number of more than 18 causes deterioration in photosensitivity and acid generation ability per molecule, any effect expected sufficiently for a used amount cannot be produced. Further, the alicyclic hydrocarbon group and the heterocyclic group may also be present in the form of being substituted with a methylene group in an alkoxy or alkylthio group, may also be present in the form of being substituted with a proton in a methylene group in an alkoxy group or an alkylthio group, or may also be present in a terminal in an alkoxy or alkylthio group.

Among the above described alkylthio groups represented by $R^2$ or $R^3$ described above, those having neither alicyclic hydrocarbon nor heterocyclic groups include the groups of which the examples are mentioned as $R^{02}$ and $R^{03}$.

Such alicyclic hydrocarbon groups and heterocyclic groups present in the above described alkylthio groups represented by $R^2$ or $R^3$ described above include the groups of which the examples are mentioned as $R^{02}$ and $R^{03}$.

Among the alkylthio groups represented by $R^2$ or $R^3$ described above, specific examples of those having alicyclic hydrocarbon groups and heterocyclic groups include the groups of which the examples are mentioned as $R^{02}$ and $R^{03}$.

Such groups which are represented by $R^2$ or $R^3$ described above and in which methylene which is not adjacent to a sulfur atom in an alkylthio group having a carbon number of 4 to 18 is substituted with —C(=O)— include the groups of which examples are mentioned as $R^{02}$ and $R^{03}$.

Further, such groups which are represented by $R^2$ or $R^3$ described above and in which the alkylthio group having a carbon number of 4 to 18 is substituted with a —O—C(=O)— bond or a —OC(=O)—NH— bond from closer proximity to a naphthalene ring includes the same as $R^{02}$ and $R^{03}$ described above.

In the above described formula (C) or (D), groups represented by $Y^4$, $Y^5$, $R^{41}$, $R^{42}$, $R^{51}$, and $R^{52}$ include the groups of which the examples are mentioned as $Y^1$, $R^{11}$, and $R^{12}$.

In the above described formula (C) or (D), alkyl groups having a carbon number of 1 to 4 and alicyclic hydrocarbon groups or heterocyclic groups having a carbon number of 3 to 10 represented by $R^{43}$ and $R^{53}$ include the groups of which the examples are mentioned as $R^{13}$.

Among the groups represented by the above described formula (C) or (D), preferred groups are those in which $R^{41}$ and $R^{51}$ are alkanediyl groups having a carbon number of 2 to 4, $R^{42}$ and $R^{52}$ are alkanediyl groups having a carbon number of 1 to 4, $R^{43}$ and $R^{53}$ are alkyl groups having a carbon number of 1 to 4, and m is 0 to 3.

Specific examples of the sulfonic acid derivative compound according to the present invention include compounds S-1 to S-78 as described below.

Compounds-1
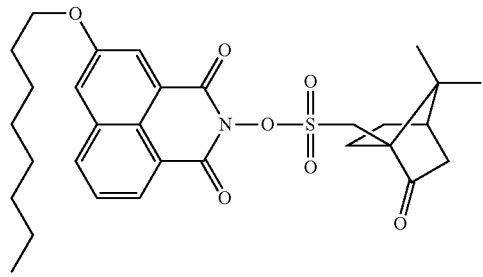

Compounds-2
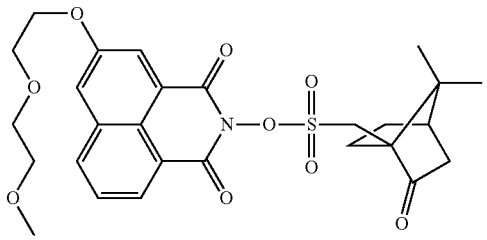

Compounds-3
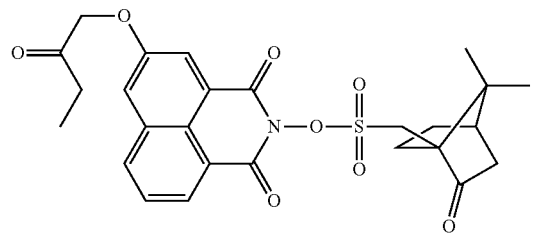

Compounds-4
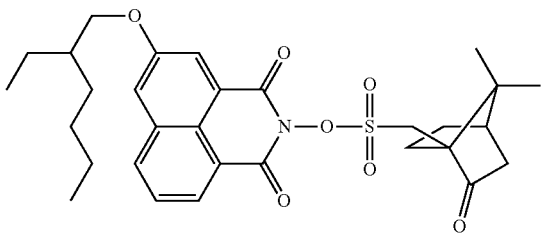

Compounds-5
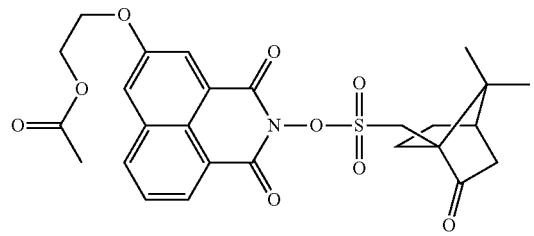

Compounds-6
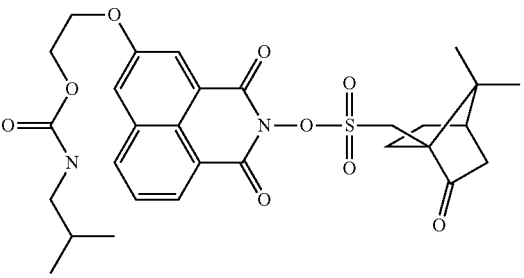

Compounds-7
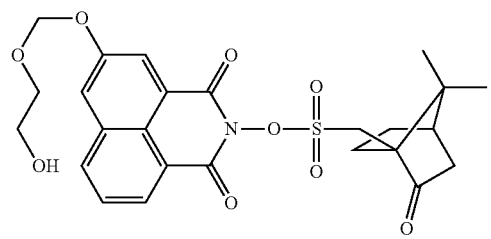

Compounds-8
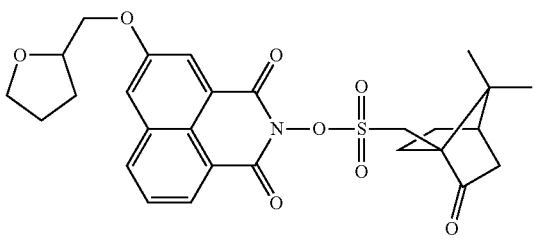

Compounds-9
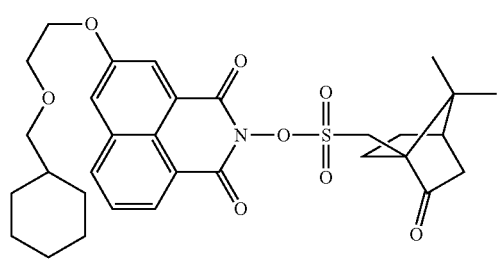

Compounds-10
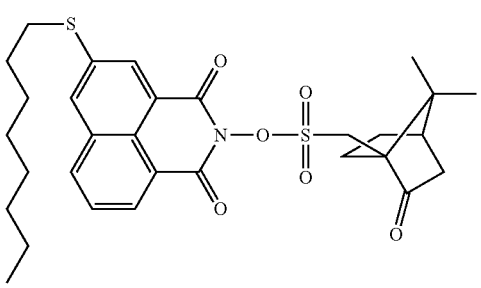

-continued
Compounds-11
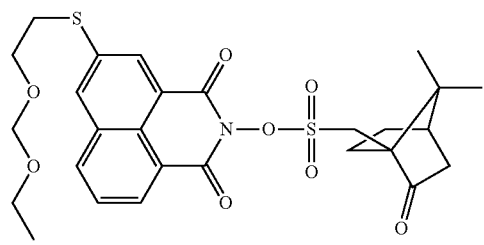
Compounds-12
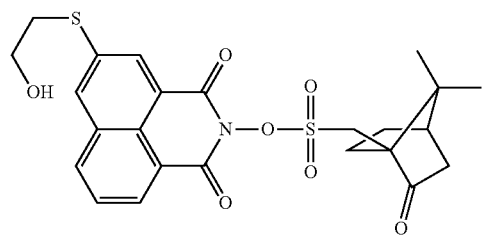
Compounds-13
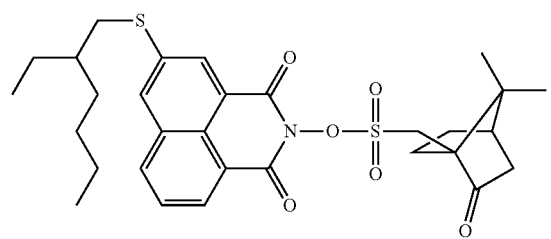
Compounds-14
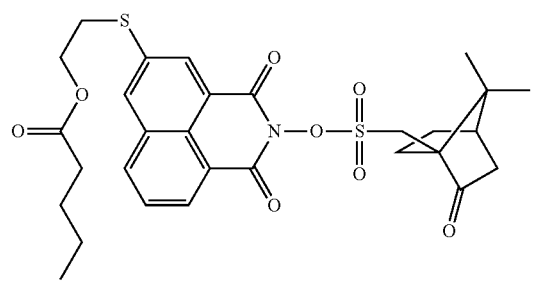
Compounds-15
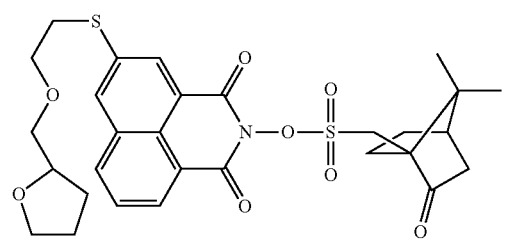
Compounds-16
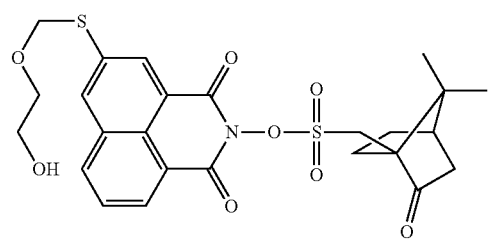
Compounds-17
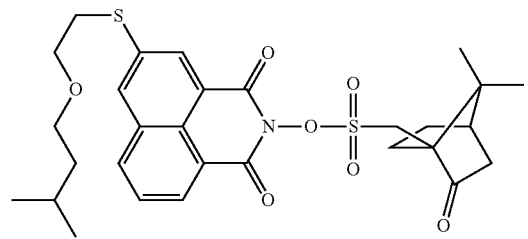
Compounds-18
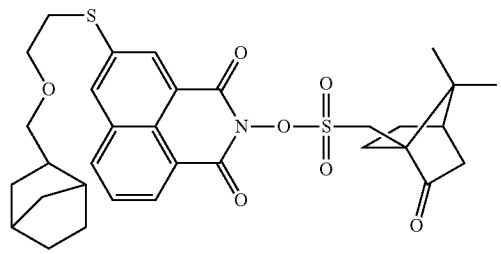
Compounds-19
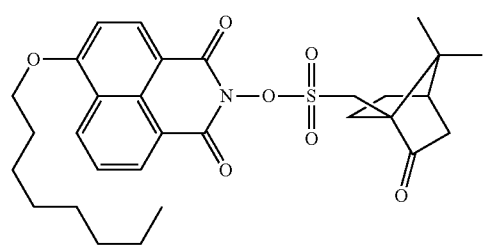
Compounds-20
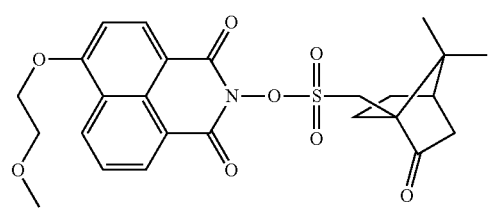

-continued
Compounds-21
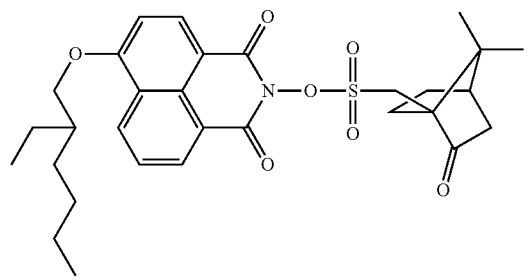
Compounds-22
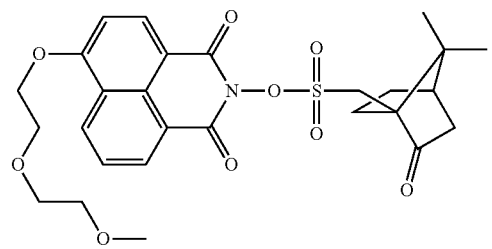
Compounds-23
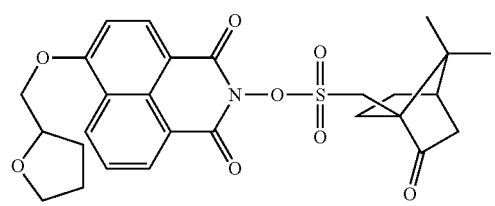
Compounds-24
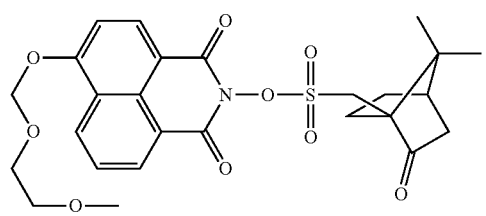
Compounds-25
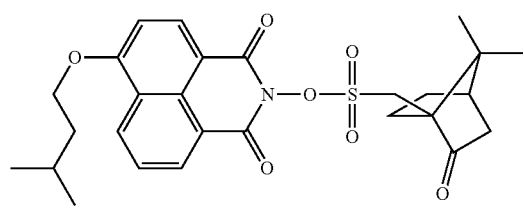
Compounds-26
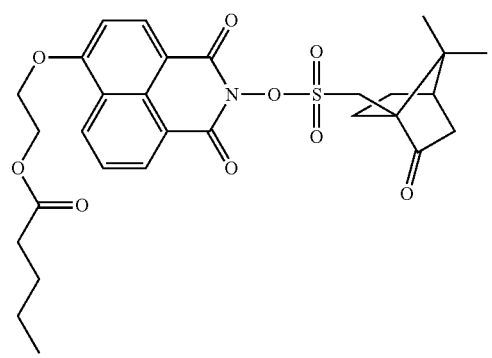
Compounds-27
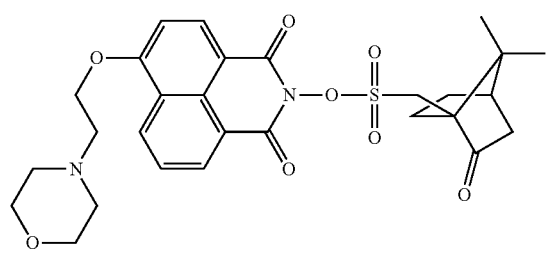
Compounds-28
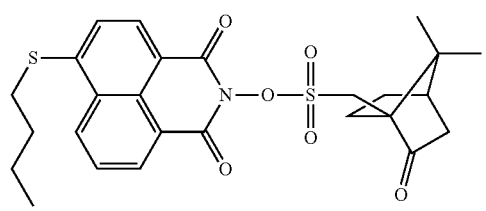
Compounds-29
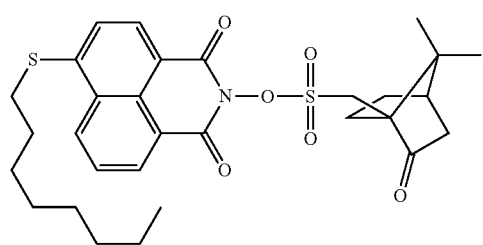
Compounds-30
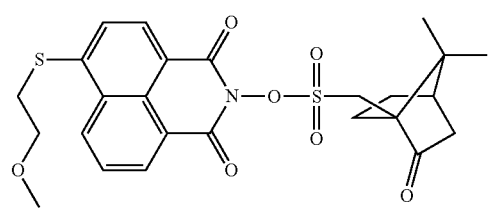

Compounds-31
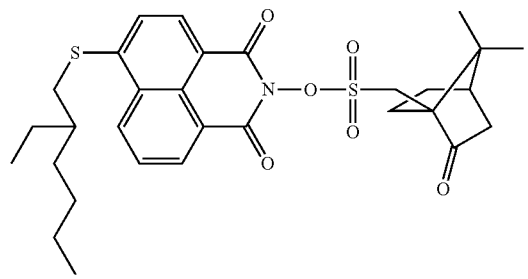
Compounds-32
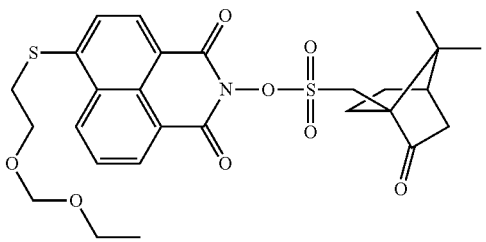
Compounds-33
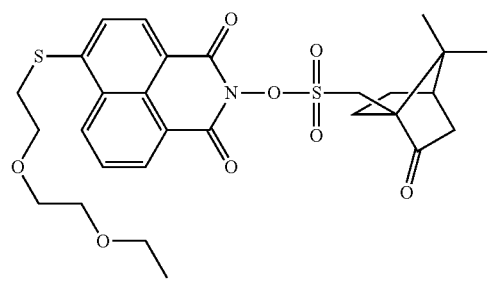
Compounds-34
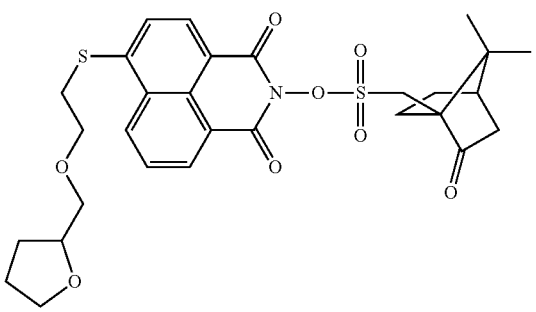
Compounds-35
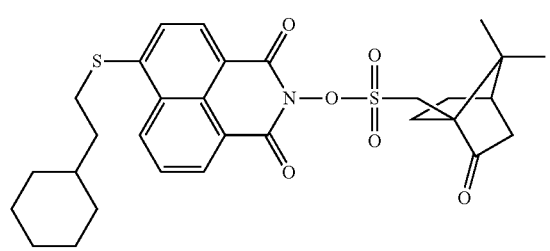
Compounds-36
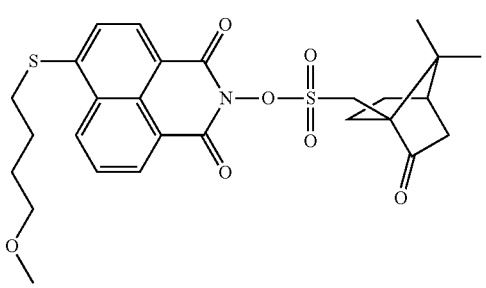
Compounds-37
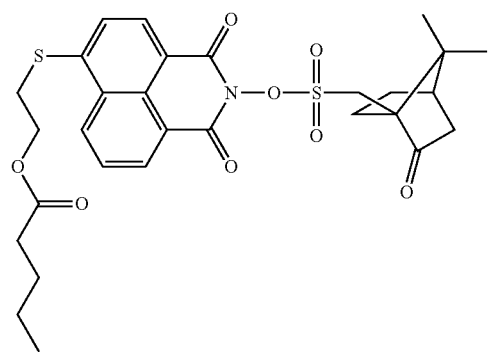
Compounds-38
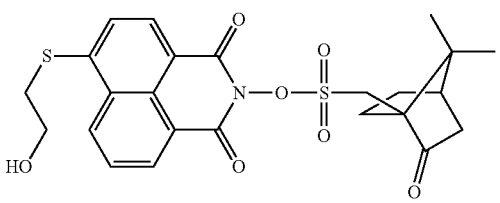
Compounds-39
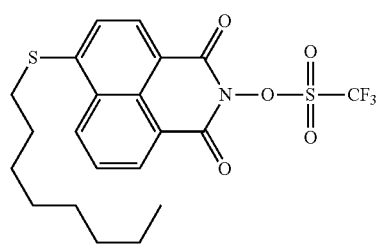
Compounds-40

-continued
Compounds-41
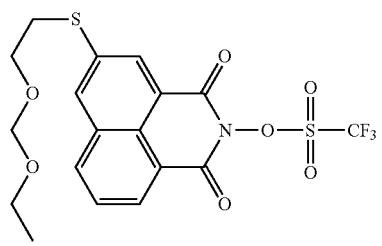
Compounds-42
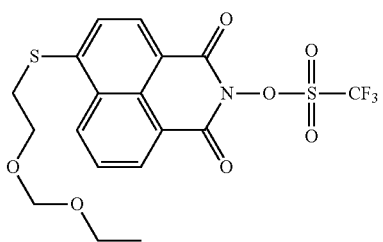
Compounds-43
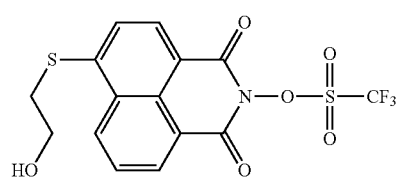
Compounds-44
Compounds-45
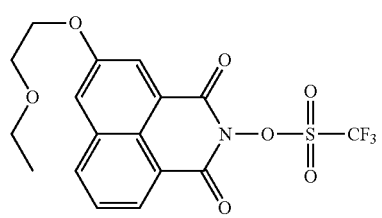
Compounds-46
Compounds-47
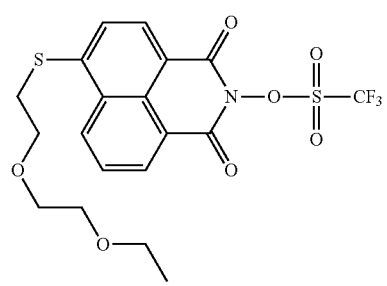
Compounds-48
Compounds-49
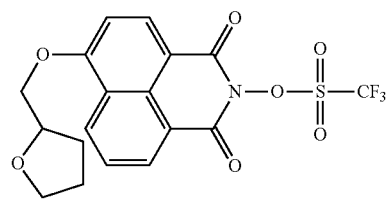
Compounds-50
Compounds-51
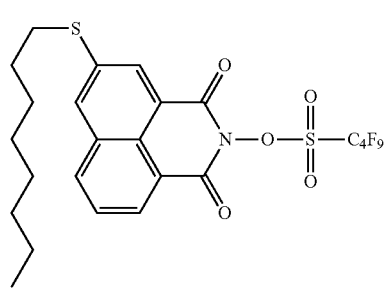
Compounds-52
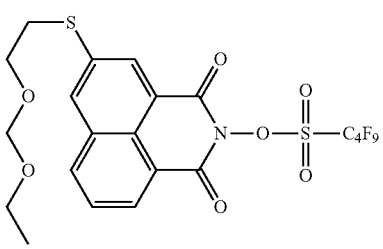

-continued
Compounds-53
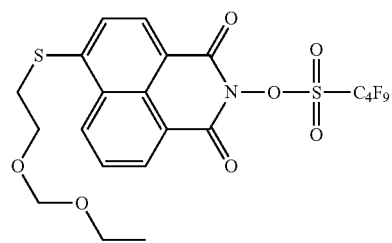
Compounds-54
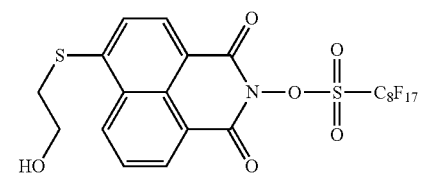
Compounds-55
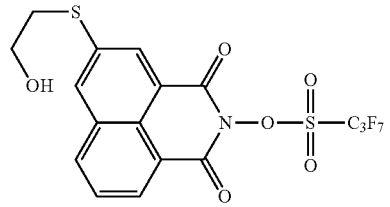
Compounds-56
Compounds-57
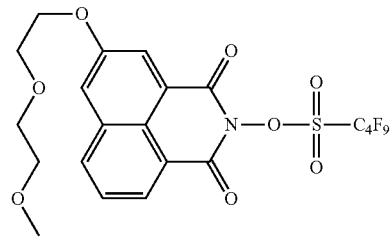
Compounds-58
Compounds-59
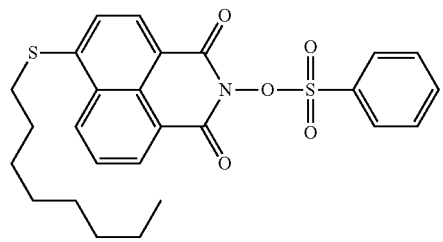
Compounds-60
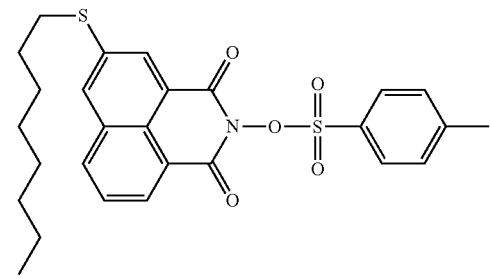
Compounds-61
Compounds-62
Compounds-63
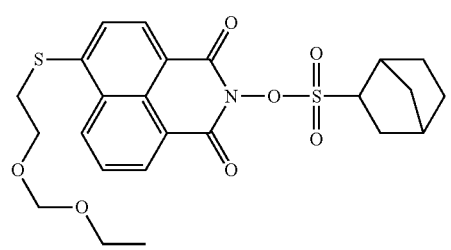
Compounds-64
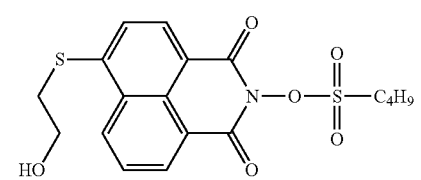

-continued
Compounds-65
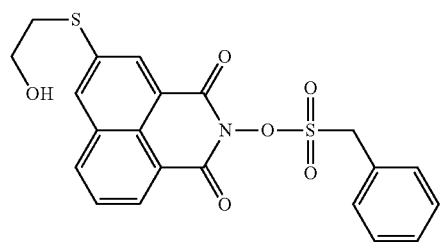
Compounds-66
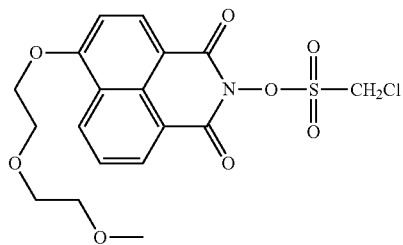
Compounds-67
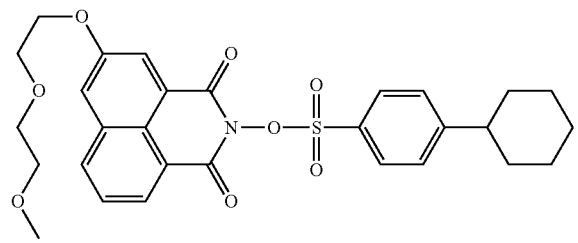
Compounds-68
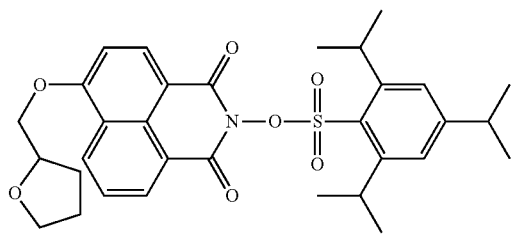
Compounds-69
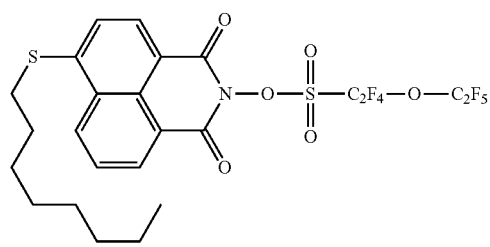
Compounds-70
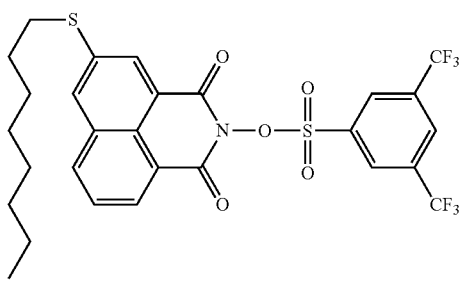
Compounds-71
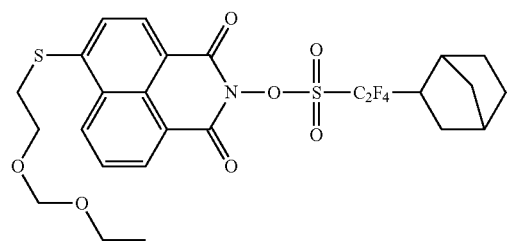
Compounds-72
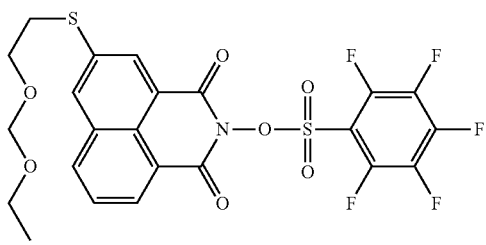
Compounds-73
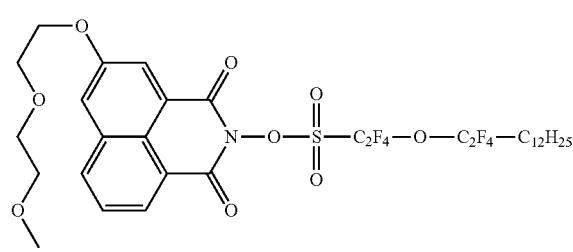
Compounds-74
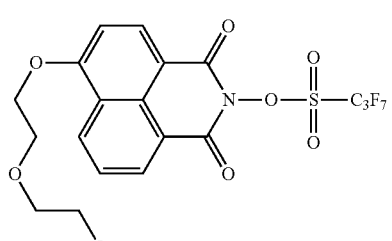
Compounds-75
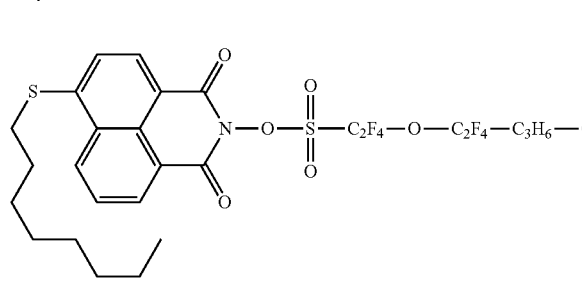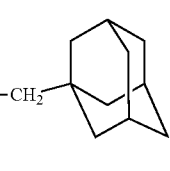

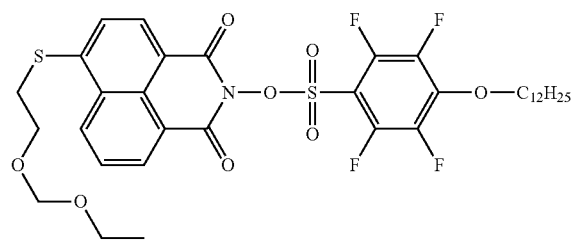
Compounds-76
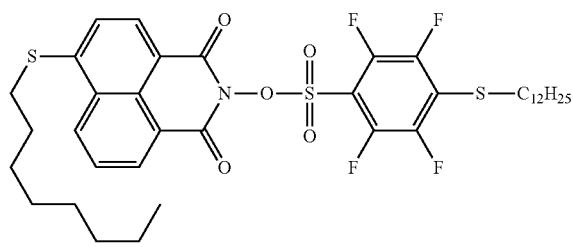
Compounds-77
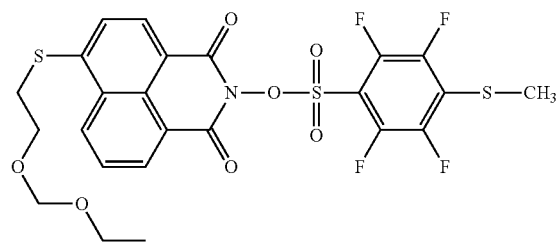
Compounds-78
Specific examples of the naphthalic acid derivative compound according to the present invention include compounds A-1 to A-9 and I-1 to I-9 as described below.
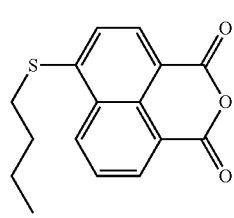
Compound A-1
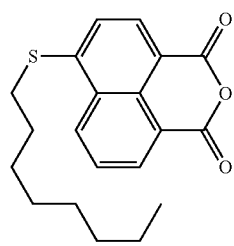
Compound A-2
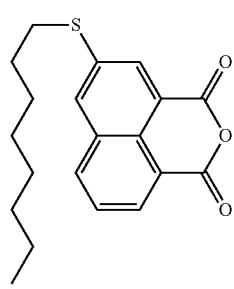
Compound A-3
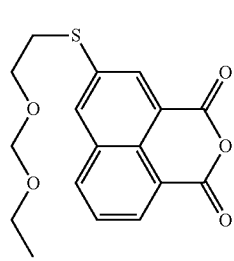
Compound A-4
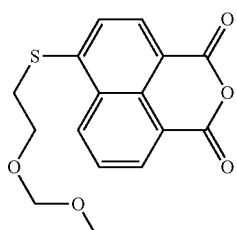
Compound A-5
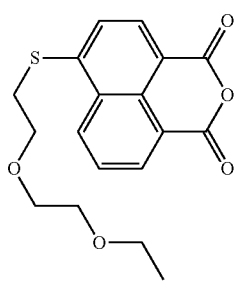
Compound A-6
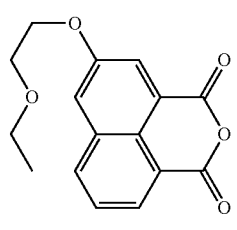
Compound A-7
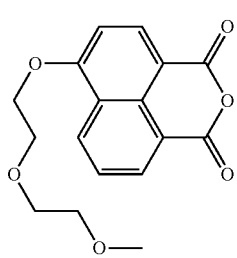
Compound A-8

Compound A-9

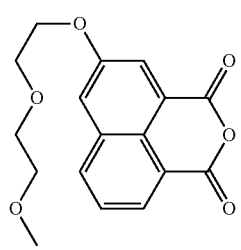

Compound I-1

Compound I-2

Compound I-3

Compound I-4

Compound I-5

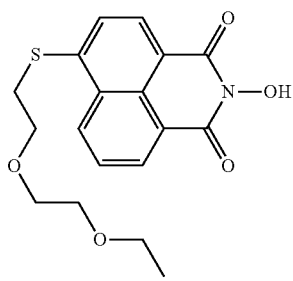

Compound I-6

Compound I-7

Compound I-8

Compound I-9

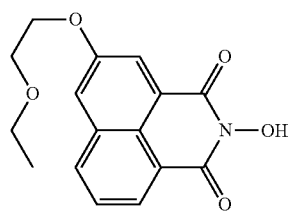

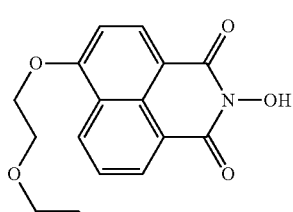

As a method for producing the sulfonic acid derivative compound and the naphthalic acid derivative compound according to the present invention, which method is not particularly limited, a well-known chemical reaction can be applied to cause synthesis. For example, routes for synthesizing the naphthalic acid derivative compound include synthesis methods with brominated compounds as described below as starting materials and methods for synthesizing phenol or thiophenol as a starting material. The method described below is a method comprising introducing a substituent into the 4-position of a naphthalic acid skeleton and one having a substituent at the 3-position can also be produced by a similar reaction.

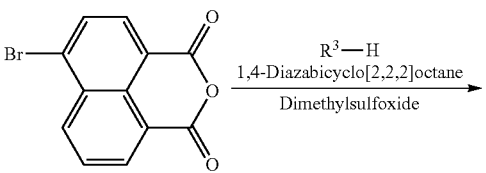

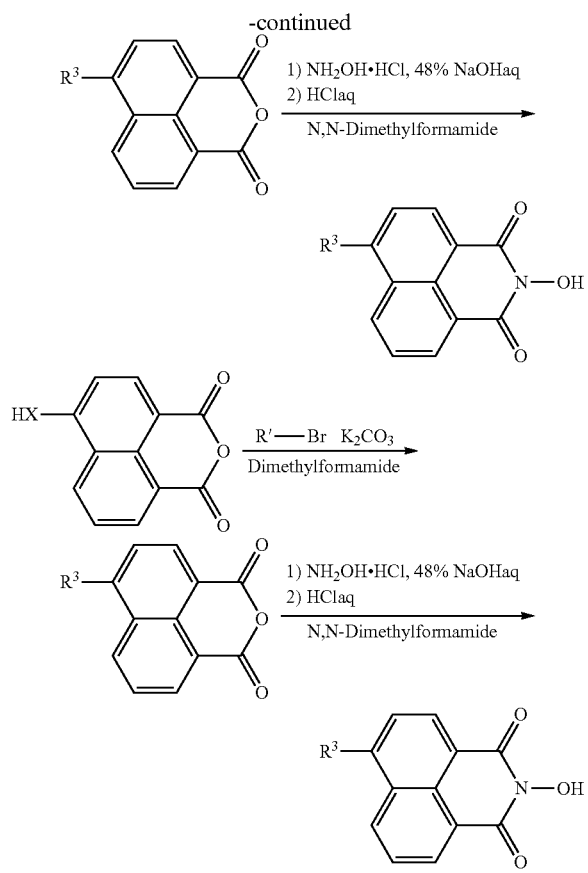

(In the formulae, $R^3$ represents the same group as in the above described formulae (II) and (III); X represents an oxygen atom or a sulfur atom; and R' represents a group bound to X to form $R^3$.)

Further, methods for synthesizing the sulfonic acid derivative compound includes a method described below.

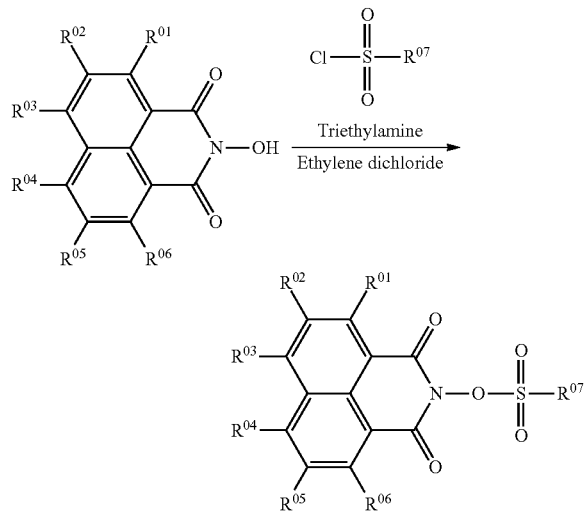

(In the formula, $R^{01}$ to $R^{07}$ represent the same groups as in the above described formula (I).)

When $R^{02}$ and $R^{03}$ described above have a —O—C(=O)— bond or a —OC(=O)—NH— bond, an alkoxy group or an alkylthio group having a hydroxyl group may be introduced into a naphthalic anhydride which is an intermediate or naphthalimide, followed by forming an ester bond or a urethane bond and reacting it with sulfonyl chloride.

The sulfonic acid derivative compound according to the present invention has the characteristic of releasing a Lewis acid by irradiation with EUV (Extreme Ultra-Violet), an x-ray, $F_2$, ArF, KrF, a far-ultraviolet ray such as i-ray, h-ray, or g-ray, or an active energy ray such as an electron beam, a radiation, or a high frequency wave and can act on an acid reactive organic substance to cause decomposition and polymerization. The sulfonic acid derivative compound according to the present invention is useful as a photoacid generator for a positive or negative photoresist and a cationic polymerization initiator for a cationically polymerizable composition.

When the sulfonic acid derivative compound according to the present invention is used in an acid reactive organic substance, the used amount thereof is not particularly limited but it is used preferably in a rate of 0.05-100 parts by mass, more preferably 0.05-20 parts by mass, based on 100 parts by mass of the acid reactive organic substance. However, it may also be used in a blending amount that is increased or decreased from the above mentioned range depending on factors such as the properties of the acid reactive organic substance, a light irradiation intensity, time required for a reaction, physical properties, and a cost.

A resin that causes change in the direction of increasing solubility in a developing solution such as cleavage of the chemical bond of an ester group, an ether group, or the like by action of an acid is used in the positive photoresist whereas a compound or a resin that causes change in the direction of decreasing solubility in a developing solution by formation of a chemical bond such as polymerization or crosslinking by action of an acid is used in the negative photoresist.

Resins or compounds which become bases for the above described resists include: polyhydroxystyrenes and derivatives thereof; polyacrylic acids and derivatives thereof; polymethacrylic acids and derivatives thereof; two or more copolymers selected and formed from hydroxystyrene, acrylic acid, methacrylic acid, and derivatives thereof; two or more copolymers selected and formed from hydroxystyrene, styrene, and derivatives thereof; three or more copolymers selected from cycloolefins and derivatives thereof; maleic anhydride, and acrylic acid and derivatives thereof; three or more copolymers selected from cycloolefins and derivatives thereof, maleimide, and acrylic acid and derivatives thereof; polynorbornene; one or more high molecular weight polymers selected from the group consisting of metathesis ring-opened polymers; high molecular weight polymers in which the high molecular weight polymers are partially substituted with an acid labile group having an alkali dissolution controlling ability; and the like. Such acid labile groups introduced into the high molecular weight polymers include tertiary alkyl groups, trialkylsilyl groups, oxoalkyl groups, aryl group-substituted alkyl groups, heterocyclic alicyclic groups such as a tetrahydropyran-2-yl group, tertiary alkylcarbonyl groups, tertiary alkylcarbonylalkyl groups, alkyloxycarbonyl groups, and the like.

Detailed specific examples of the resins or the compounds which becomes bases for such resists are disclosed in, for example, Japanese Unexamined Patent Application Publication No. 2003-192665, claim 3 in Japanese Unexamined Patent Application Publication No. 2004-323704, and Japanese Unexamined Patent Application Publication No. 10-10733.

Further, the polystyrene equivalent weight average molecular weight (Mw) of a resin which becomes a base for the above described resists by gel permeation chromatography (GPC) is typically 1,500 to 300,000, preferably 2,000 to 200,000, more preferably 3,000 to 100,000. In this case, thermal resistance as the resists tends to deteriorate when the Mw of the base resin is less than 1,500 while developability and application properties as the resists tend to deteriorate when it is more than 300,000.

The used amount of the sulfonic acid derivative compound according to the present invention when it is used as a photoacid generator in a photoresist composition is typically 0.01-20 parts by mass, preferably 0.5-10 parts by mass, based on 100 parts by mass of a resist base resin or compound from the viewpoint of ensuring sensitivity and developability as a photoresist. In this case, the sensitivity and the developability may be deteriorated when the amount of the photoacid generator used is less than 0.01 part by mass whereas transparency to radiation may be deteriorated to inhibit a rectangular resist pattern from being obtained when the amount is more than 20 parts by mass.

When the sulfonic acid derivative compound according to the present invention is used as a photoacid generator, it may be combined with another photoacid generator such as an iodonium salt compound or a sulfonium compound. The used amount thereof when it is combined is preferably 10-200 parts by mass based on 100 parts by mass of the sulfonic acid derivative compound according to the present invention.

A photoresist in which the sulfonic acid derivative compound according to the present invention is used as a photoacid generator may be blended with various additives. Various additives include various resin additives such as inorganic fillers, organic fillers, coloring agents such as pigments and dyes, antifoaming agents, thickeners, fire retardants, antioxidants, stabilizers, and leveling agents. The amount of the various additives used is preferably 50 mass % or less in total in the photoresist composition in which the sulfonic acid derivative compound according to the present invention is used as the photoacid generator.

The above described photoresist is typically adjusted by being dissolved in a solvent to have a total solid concentration of typically 5-50% by weight, preferably 10-25% by weight, and thereafter being filtered through, for example, a filter with a bore diameter of around 0.2 μm, when it is used.

A light source used in exposure of the above described photoresist to light is appropriately selected and used from visible light rays, ultraviolet rays, near-ultraviolet rays, far-ultraviolet rays, x-rays, charged particle beams, and the like depending on the kind of an acid generator used; and various radiations such as near-ultraviolet rays such as a KrF excimer laser (wavelength of 248 nm), far-ultraviolet rays such as an ArF excimer laser (193 nm), x-rays such as synchrotron radiations, and charged particle beams such as electron beams and EUV can preferably be used for the sulfonic acid derivative compound according to the present invention.

The cationically polymerizable composition is used in printing matrices for laser lithography, lithography, and letterpress, formation of images such as relief images and replicated images, photo-curable inks, paints, adhesive printed circuit boards, and the like.

In the cationically polymerizable composition, one or two or more cationically polymerizable compounds which cause polymerization or a crosslinking reaction by a cationic polymerization initiator activated by light irradiation are mixed and used.

Representative cationically polymerizable compounds are epoxy compounds, oxetane compounds, cyclic lactone compounds, cyclic acetal compounds, cyclic thioether compounds, spiroorthoester compounds, vinyl compounds, and the like, and one or two or more thereof may be used. Especially, the epoxy compounds and the oxetane compounds which are easily obtained and conveniently handled are suitable.

As the epoxy compounds among them, alicyclic epoxy compounds, aromatic epoxy compounds, aliphatic epoxy compounds, and the like are suitable.

Specific examples of the above described alicyclic epoxy compounds include the polyglycidyl ethers of polyhydric alcohols having at least one alicyclic ring or cyclohexene oxide- and cyclopentene oxide-containing compounds obtained by epoxidation of cyclohexene and cyclopentene ring-containing compounds with an oxidizing agent. For example, mentions is made of hydrogenated bisphenol-A diglycidyl ether, 3,4-epoxycyclohexylmethyl-3,4-epoxycyclohexanecarboxylate, 3,4-epoxy-1-methylcyclohexyl-3,4-epoxy-1-methylcyclohexanecarboxylate, 6-methyl-3,4-epoxycyclohexylmethyl-6-methyl-3,4-epoxycyclohexanecarboxylate, 3,4-epoxy-3-methylcyclohexylmethyl-3,4-epoxy-3-methylcyclohexanecarboxylate, 3,4-epoxy-5-methylcyclohexylmethyl-3,4-epoxy-5-methylcyclohexanecarboxylate, 2-(3,4-epoxycyclohexyl-5,5-spiro-3,4-epoxy)cyclohexane-metadioxane, bis(3,4-epoxycyclohexylmethyl)adipate, 3,4-epoxy-6-methylcyclohexylcarboxylate, methylenebis(3,4-epoxycyclohexane), dicyclopentadiene diepoxide, ethylenebis(3,4-epoxycyclohexanecarboxylate), dioctyl epoxyhexahydrophthalate, di-2-ethylhexyl epoxyhexahydrophthalate, and the like.

Commercially available products which may preferably be used as the above described alicyclic epoxy resins may include UVR-6100, UVR-6105, UVR-6110, UVR-6128, and UVR-6200 (all of these are manufactured by Union Carbide Corporation); Celloxide 2021, Celloxide 2021P, Celloxide 2081, Celloxide 2083, Celloxide 2085, Celloxide 2000, Celloxide 3000, Cyclomer A200, Cyclomer M100, Cyclomer M101, Epolead GT-301, Epolead GT-302, Epolead 401, Epolead 403, ETHB, and Epolead HD300 (all of these are manufactured by Daicel Chemical Industries, Ltd.); KRM-2110 and KRM-2199 (both of these are manufactured by ADEKA Corporation); and the like.

Among the above described alicyclic epoxy resins, those having a cyclohexane oxide structure are preferred in terms of curability (curing rate).

Specific examples of the above described aromatic epoxy resins include polyphenols having at least one aromatic ring, polyglycidyl ethers of its alkylene oxide adduct, such as bispenol A and bisphenol F, glycidyl ethers and epoxy novolac resins of compounds prepared by further addition of alkylene oxide to them, or the like.

Furthermore, specific examples of the above described aliphatic epoxy resins include aliphatic polyhydric alcohols or polyglycidyl ethers of their alkylene oxide adducts; polyglycidyl esters of aliphatic long-chain polybasic acids; homopolymers synthesized by vinyl polymerization of glycidyl acrylate or glycidyl methacrylate; copolymers synthesized by vinyl polymerization of glycidyl acrylate or glycidyl methacrylate with other vinyl monomers; and the like. The representative compounds include glycidyl ethers of polyhydric alcohols such as 1,4-butanediol diglycidyl ether, 1,6-hexanediol diglycidyl ether, triglycidyl ethers of glycerol, triglycidyl ethers of trimethylolpropane, tetraglycidyl ethers of sorbitol, hexaglycidyl ethers of dipentaerythritol, diglycidyl ethers of polyethylene glycol, and diglycidyl ethers of polypropylene glycol; polyglycidyl ethers of polyether polyols obtained by addition of one or two or more alkylene oxides to aliphatic polyhydric alcohols such as propylene glycol, trimethylolpropane, and glycerol; and diglycidyl esters of aliphatic long-chain dibasic acids. Furthermore, mentions is made of monoglycidyl ethers of aliphatic higher alcohols; monoglycidyl ethers of phenol, cresol, butylphenol, and polyether alcohols obtained by addition of alkylene oxide to them; glycidyl esters of higher fatty acids; epoxidized soybean oils; epoxy octyl stearate; epoxy butyl stearate; epoxidized polybutadienes; and the like.

Commercially available products which may preferably be used as the above described aromatic and aliphatic epoxy resins may include Epikote 801 and Epikote 828 (both of these are manufactured by Yuka Shell Epoxy K.K.); PY-306, 0163, and DY-022 (all of these are manufactured by Ciba Specialty Chemicals Inc.); KRM-2720, EP-4100, EP-4000, EP-4080, EP-4900, ED-505, and ED-506 (all of these are manufactured by ADEKA Corporation); Epolight M-1230, Epolight EHDG-L, Epolight 40E, Epolight 100E, Epolight 200E, Epolight 400E, Epolight 70P, Epolight 200P, Epolight 400P, Epolight 1500NP, Epolight 1600, Epolight 80MF, Epolight 100MF, Epolight 4000, Epolight 3002, and Epolight FR-1500 (all of these are manufactured by Kyoeisha Chemical Co., Ltd.); Sun Tohto ST0000, YD-716, YH-300, PG-202, PG-207, YD-172, and YDPN638 (all of these are manufactured by Tohto Kasei Co., Ltd.); and the like.

Further, specific examples of the above described oxetane compounds may include, for example, the following compounds: 3-ethyl-3-hydroxymethyloxetane, 3-(meth)allyloxymethyl-3-ethyloxetane, (3-ethyl-3-oxetanylmethoxy)methylbenzene, 4-fluoro-[1-(3-ethyl-3-oxetanylmethoxy), ethyl]benzene, 4-methoxy-[1-(3-ethyl-3-oxetanylmethoxy)methyl]benzene, [1-(3-ethyl-3-oxetanylmethoxy)ethyl]phenylether, isobutoxymethyl(3-ethyl-3-oxetanylmethyl)ether, isobornyloxyethyl(3-ethyl-3-oxetanylmethyl)ether, isobornyl(3-ethyl-3-oxetanylmethyl)ether, 2-ethylhexyl(3-ethyl-3-oxetanylmethyl)ether, ethyldiethyleneglycol(3-ethyl-3-oxetanylmethyl)ether, dicyclopentadiene(3-ethyl-3-oxetanylmethyl)ether, dicyclopentenyloxyethyl(3-ethyl-3-oxetanylmethyl)ether, dicyclopentenyl(3-ethyl-3-oxetanylmethyl)ether, tetrahydrofurfuryl(3-ethyl-3-oxetanylmethyl)ether, tetrabromophenyl(3-ethyl-3-oxetanylmethyl)ether, 2-tetrabromophenoxyethyl(3-ethyl-3-oxetanylmethyl)ether, tribromophenyl(3-ethyl-3-oxetanylmethyl)ether, 2-tribromophenoxyethyl(3-ethyl-3-oxetanylmethyl)ether, 2-hydroxyethyl(3-ethyl-3-oxetanylmethyl)ether, 2-hydroxypropyl(3-ethyl-3-oxetanylmethyl)ether, butoxyethyl(3-ethyl-3-oxetanylmethyl)ether, pentachlorophenyl(3-ethyl-3-oxetanylmethyl)ether, pentabromophenyl(3-ethyl-3-oxetanylmethyl)ether, bornyl(3-ethyl-3-oxetanylmethyl)ether, 3,7-bis(3-oxetanyl)-5-oxa-nonane, 3,3'-(1,3-(2-methylenyl)propanediyl bis(oxymethylene))bis-(3-ethyloxetane), 1,4-bis[(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethylene glycol bis(3-ethyl-3-oxetanylmethyl)ether, dicyclopentenyl bis(3-ethyl-3-oxetanylmethyl)ether, triethylene glycol bis(3-ethyl-3-oxetanylmethyl)ether, tetraethylene glycol bis(3-ethyl-3-oxetanylmethyl)ether, tricyclodecanediyldimethylene(3-ethyl-3-oxetanylmethyl)ether, trimethylolpropane tris(3-ethyl-3-oxetanylmethyl)ether, 1,4-bis(3-ethyl-3-oxetanylmethoxy)butane, 1,6-bis(3-ethyl-3-oxetanylmethoxy)hexane, pentaerythritol tris(3-ethyl-3-oxetanylmethyl)ether, pentaerythritol tetrakis(3-ethyl-3-oxetanylmethyl)ether, polyethylene glycol bis(3-ethyl-3-oxetanylmethyl)ether, dipentaerythritol hexakis(3-ethyl-3-oxetanylmethyl)ether, dipentaerythritol pentakis(3-ethyl-3-oxetanylmethyl)ether, dipentaerythritol tetrakis(3-ethyl-3-oxetanylmethyl)ether, caprolactone-modified dipentaerythritol hexakis(3-ethyl-3-oxetanylmethyl)ether, caprolactone-modified dipentaerythritol pentakis(3-ethyl-3-oxetanylmethyl)ether, ditrimethylolpropane tetrakis(3-ethyl-3-oxetanylmethyl)ether, EO-modified bispenol A bis(3-ethyl-3-oxetanylmethyl)ether, PO-modified bispenol A bis(3-ethyl-3-oxetanylmethyl)ether, EO-modified hydrogenated bispenol A bis(3-ethyl-3-oxetanylmethyl)ether, PO-modified hydrogenated bispenol A bis(3-ethyl-3-oxetanylmethyl)ether, EO-modified bisphenol F(3-ethyl-3-oxetanylmethyl)ether, and the like.

Use of these oxetane compounds is effective and preferable especially when flexibility is required.

Specific examples of other compounds for the above described cationically polymerizable compound include well-known compounds including cyclic lactone compounds such as β-propiolactone and ε-caprolactone; cyclic acetal compounds such as trioxane, 1,3-dioxolane, and 1,3,6-trioxanecyclooctane; cyclic thioether compounds such as tetrahydrothiophene derivatives; spiroorthoester compounds obtained by reaction of the above mentioned epoxy compounds with lactone; vinyl ether compounds such as ethylene glycol divinyl ether, alkyl vinyl ether, 2-chloroethyl vinyl ether, 2-hydroxyethyl vinyl ether, triethylene glycol divinyl ether, 1,4-cyclohexanedimethanol divinyl ether, hydroxybutyl vinyl ether, and the propenyl ether of propylene glycol; vinyl compounds such as ethylenically unsaturated compounds such as styrene, vinylcyclohexene, isobutylene, and polybutadiene; oxolane compounds such as tetrahydrofuran and 2,3-dimethyltetrahydrofuran; thiirane compounds such as ethylene sulfide and thioepichlorohydrin; thietane compounds such as 1,3-propyne sulfide and 3,3-dimethylthietane; silicones; and the like.

The used amount of the sulfonic acid derivative compound according to the present invention which is used as a cationic polymerization initiator is preferably 0.01 part by mass to 10 parts by mass, more preferably 0.1 part by mass to 5 parts by mass, based on 100 parts by mass of the above described cationically polymerizable compound. Curing may be insufficient when the used amount is less than 0.01 part by mass whereas not only the effect of its usage cannot be increased but also it may adversely affect the physical properties of the cured product even when the amount is more than 10 parts by mass.

Further, the sulfonic acid derivative compound according to the present invention is used as a cationically polymerizable composition which is blended with various additives as well as the above described cationically polymerizable compound. The various additives include organic solvents; benzotriazole, triazine, and benzoate ultraviolet absorbers; phenolic, phosphorus, and sulfur antioxidants; antistatic agents comprising cationic surfactants, anionic surfactants, nonionic surfactants, ampholytic surfactants, and the like; flame retardants such as halogen compounds, phosphate ester compounds, phosphoric amide compounds, melamine compounds, fluorine resins or metal oxides, (poly)melamine phosphate, and (poly)piperazine phosphate; hydrocarbon, aliphatic acid, aliphatic alcohol, aliphatic ester, aliphatic amide, or metal soap lubricants; coloring agents such as dyes, pigments, and carbon black; inorganic silica additives such as fumed silica, microparticulate silica, silica rock, diatomaceous earth, clay, kaolin, diatomaceous earth, silica gel, calcium silicate, sericite, kaolinite, flint, feldspar powder, vermiculite, attapulgite, talc, mica, minnesotaite, pyrophyllite, and silica; fillers such as glass fibers and calcium carbonate; crystallization agents such as nucleating agents and crystallization-promoting agents, silane coupling agents, rubber elasticity granting agents such as flexible polymers, sensitizers, and the like. The amount of these various additives used is 50 mass % or less in total in the cationically polymerizable composition comprising the sulfonic acid derivative compound according to the present invention.

Further, in order to facilitate dissolution of the sulfonic acid derivative according to the present invention in the above described cationically polymerizable compound, it may previously be dissolved in an appropriate solvent (e.g., propylene carbonate, carbitol, carbitol acetate, butyrolactone, or the like) and used.

The above described cationically polymerizable composition can be cured in a dry-to-touch state or a solvent-insoluble state typically after 0.1 second to several minutes by being irradiated with energy rays such as ultraviolet rays. As appropriate energy rays, any energy rays may be used as long as decomposition of a cationic polymerization initiator is induced, and, preferably, electromagnetic wave energies having wavelengths of from 2,000 angstroms to 7,000 angstroms obtained from extra-high, high, medium, and low pressure mercury lamps, xenon lamps, carbon-arc lamps, metal halide lamps, fluorescent lamps, tungsten lamps, excimer lamps, germicidal lamps, excimer lasers, nitrogen lasers, argon ion lasers, helium-cadmium lasers, helium-neon lasers, krypton ion lasers, various semiconductor lasers, YAG lasers, light emitting diodes, CRT light sources, and the like, and high energy rays such as electron beams, x-rays, and radiations are utilized.

Time of exposure to an energy ray, which time depends on the intensity of the energy ray, a film thickness, and cationically polymerizable organic compound, is typically sufficiently around 0.1 second to 10 seconds. However, longer irradiation time than the time is preferred for a relatively thick article to be painted. By cationic polymerization, most of compositions are dried to touch 0.1 second to several minutes after the irradiation with the energy rays, and thermal energy by heating, thermal head, or the like is also preferably used together in some cases to accelerate the cationic polymerization.

EXAMPLES

Examples 1, 4, 7, 10, and 15 below describe examples of production of the naphthalic acid derivative compound according to the present invention represented by the formula (II); Examples 2, 5, 8, 11, and 16 describe examples of production of the naphthalic acid derivative compound according to the present invention represented by the formula (III); and Examples 3, 6, 9, 12, 13, 14, 17, 18, and 19 describe examples of production of the sulfonic acid derivative compound according to the present invention.

Example 1

Production of Compound A-1

In a 100 ml four-neck flask, 9.290 g (0.0335 mol) of 4-bromonaphthalic anhydride, 34.0 g of dimethyl sulfoxide, and 4.140 g (0.0369 mol) of 1,4-diazabicyclo[2.2.2]octane were put and stirred, and the atmosphere in the system was replaced with nitrogen gas. Dropwise added was 3.170 g (0.0352 mol) of butanthiol at 30° C. or less, and the resultant was stirred at 40° C. for 5 hours. Into the reaction liquid, 70 ml of methanol was put, the resultant was ice-cooled and stirred for 30 minutes, and precipitated crystals were filtered off. By drying them, the compound A-1 which was a target was yielded as a yellow crystal. Yield: 7.15 g (yield: 74.6%), purity: 97.4% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm). The measurement results of $^1$H-NMR by a deuterated dimethyl sulfoxide solvent are listed in Table 1-1.

Example 2

Production of Compound I-1

In a 100 ml four-neck flask, 6.87 g (0.0240 mol) of the compound A-1, 27.5 g of dimethylformamide, and 2.00 g (0.0288 mol) of hydroxylamine hydrochloride were put and stirred, and the atmosphere in the system was replaced with nitrogen gas. Dropwise added was 2.40 g (0.0288 mol) of 48% by weight aqueous sodium hydroxide solution at 30° C. or less, and the resultant was stirred at room temperature for 2 hours. Into the reaction liquid, 27.5 ml of deionized water was put, the resultant was ice-cooled and stirred for 30 minutes, 1.00 g (0.0096 mol) of 35% by weight aqueous hydrochloric acid solution was put, and the resultant was stirred for 1 hour. Precipitated crystals were filtered off and, by drying them, the compound I-1 which was a target was yielded as a yellow crystal. Yield: 7.04 g (yield: 97.4%), purity: 98.1% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm). The measurement results of $^1$H-NMR by a deuterated dimethyl sulfoxide solvent are listed in Table 1-1.

Example 3

Production of Compound S-28

In a 50 ml four-neck flask, 3.01 g (0.0100 mol) of the compound I-1, 17.7 g of ethylene dichloride, and 1.26 g (0.0125 mol) of triethylamine were put, stirred, and dissolved, followed by replacing the atmosphere in the system with nitrogen gas. Dropwise added was 5.77 g (0.0110 mol) of a solution of 48 mass % d-camphor sulfonyl chloride in ethylene dichloride at 20° C., and the resultant was stirred for 2 hours. To the reaction liquid, 20 ml of deionized water and 10 ml of methylene chloride were added, stirred, and subjected to oil-water separation to yield the organic layer, which was washed twice with 20 ml of 0.5% by weight aqueous sodium hydroxide solution, once with 20 ml of 3% by weight aqueous hydrochloric acid solution, and four times with 30 ml of deionized water, followed by distilling off the solvent from the methylene chloride layer to yield a target as a yellow solid. Yield: 4.696 g (yield: 90.9%), purity: 95.4% by HPLC (column: CAPCELL PAK C8 DD manufactured by Shiseido Company, Limited, 4.6 mm×250 mm, solvent: acetonitrile/water=7/3, L-7455 diode array detector manufactured by Hitachi, Ltd., detection wavelength: 230 nm). The measurement results of $^1$H-NMR by a deuterated chloroform solvent are listed in Table 1-1. The measurement results of MALDI TOF-MS (m/z) were 538.4 (sodium ion adduct) and 554.4 (potassium ion adduct).

Example 4

Production of Compound A-2

In a 100 ml four-neck flask, 11.08 g (0.0400 mol) of 4-bromonaphthalic anhydride, 33.24 g of dimethyl sulfoxide, and 5.18 g (0.0462 mol) of 1,4-diazabicyclo[2.2.2]octane were put and stirred, followed by replacing the atmosphere in the system with nitrogen gas. Dropwise added was 6.14 g (0.0420 mol) of 1-octanethiol at 30° C. or less, and the resultant was stirred at 40° C. for 4 hours. The reaction system was cooled to room temperature, 400 ml of ethyl acetate and 100 ml of deionized water were added and subjected to oil-water separation to yield the ethyl acetate layer, which was washed four times with 100 ml of deionized water, followed by distilling off ethyl acetate, adding 20 ml of diisopropyl ether, performing crystallization to yield crystals, which were filtered off and dried to yield the compound A-2 which was a target as a yellow crystal. Yield: 6.04 g (yield: 44.1%). Purity: 94.1% by HPLC (column: CAPCELL PAK C8 DD manufactured by Shiseido Company, Limited, 4.6 mm×250 mm, solvent: acetonitrile/water=8/2, L-7455 diode array detector manufactured by Hitachi, Ltd., detection wavelength: 230 nm). The measurement results of $^1$H-NMR by a deuterated acetone solvent are listed in Table 1-1.

Example 5

Production of Compound I-2

In a 100 ml four-neck flask, 5.82 g (0.0170 mol) of the compound A-2, 1.30 g (0.0187 mol) of hydroxylamine hydrochloride, and 23.29 g of N,N-dimethylformamide were put and stirred, followed by replacing the atmosphere in the system with nitrogen gas. Dropwise added was 1.56 g (0.0187 mol) of 48 mass % aqueous sodium hydroxide solution at 30° C., and the resultant was stirred at 50° C. for 3 hours. It was cooled to room temperature, followed by loading 24 ml of deionized water and 0.71 g (0.0068 mol) of 35 mass % hydrochloric acid and stirring the resultant for 1 hour. It was filtered of to yield crystals, which were dried to yield the compound I-2 which was a target as a yellow crystal. Yield: 5.56 g (yield: 91.5%). Purity: 98.6% by HPLC (column: CAPCELL PAK C8 DD manufactured by Shiseido Company, Limited, 4.6 mm×250 mm, solvent: acetonitrile/water=8/2, L-7455 diode array detector manufactured by Hitachi, Ltd., detection wavelength: 230 nm). The measurement results of $^1$H-NMR by a deuterated acetone solvent are listed in Table 1-1.

Example 6

Production of Compound S-29

In a 50 ml four-neck flask, 3.57 g (0.0100 mol) of the compound I-2, 14.3 g of ethylene dichloride, and 1.26 g (0.0125 mol) of triethylamine were put, stirred, and dissolved, followed by replacing the atmosphere in system with nitrogen gas. Dropwise added was 5.77 g (0.0110 mol) of a solution of 48 mass % d-camphor sulfonyl chloride in ethylene dichloride at 26° C., and the resultant was stirred for 1 hour. To the reaction liquid, 140 ml of 0.5 mass % aqueous sodium hydroxide solution and 70 ml of methylene chloride were added, stirred, and subjected to oil-water separation to yield the methylene chloride layer, which was washed once with 30 ml of deionized water, thereafter made to have a pH of 2 with 30 ml of deionized water and 35 mass % hydrochloric acid, and further washed three times with 30 ml of deionized water. The solvent was distilled off from the methylene chloride layer to yield 5.62 g of the crude product of a brown viscous body. It was subjected to purification by silica gel chromatogram (developing solvent with a hexane-to-ethyl acetate volume ratio of 5-3 (hexane):1 (ethyl acetate)) to yield the compound S-29 which was a target as a yellow solid.

Yield: 4.65 g (yield: 81.3%), purity: 97.8% by HPLC (column: CAPCELL PAK C8 DD manufactured by Shiseido Company, Limited, 4.6 mm×250 mm, solvent: acetonitrile/water=8/2, L-7455 diode array detector manufactured by Hitachi, Ltd., detection wavelength: 230 nm). The measurement results of $^1$H-NMR by a deuterated acetone solvent are listed in Table 1-1. The measurement results of MALDI TOF-MS (m/z) were 594.5 (sodium ion adduct) and 610.5 (potassium ion adduct).

Example 7

Production of Compound A-5

In a 100 ml four-neck flask, 11.08 g (0.0400 mol) of 4-bromonaphthalic anhydride, 5.54 g (0.0490 mol) of 1,4-diazabicyclo[2.2.2]octane, and 40.00 g of dimethyl sulfoxide were put and stirred, followed by replacing the atmosphere in the system with nitrogen gas. To this, 3.68 g (0.0470 mol) of 2-mercaptoethanol was dropwise added at 28° C. and stirred at room temperature for 6 hours, 20 ml of deionized water was thereafter added at 30° C. or less and stirred for 20 minutes, and precipitated crystals were filtered off. By drying them, 4-(2-hydroxyethylthio)naphthalic anhydride which was an intermediate was yielded as a yellow crystal. Yield: 8.88 g (yield: 80.9%), purity: 98.0% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm).

In a 500 ml four-neck flask, 8.23 g (0.0300 mol) of the above described intermediate, 200 g of acetonitrile, and 21.73 g (0.1110 mol) of ethoxymethyl triethylammonium chloride were put and stirred, followed by replacing the atmosphere in the system with nitrogen gas. Then, the resultant was refluxed at 80° C. for 4 hours. The cooled reaction liquid was transferred to a 500 ml egg-type flask and subjected to vacuum concentration to be 37.8 g, and 80 ml of methylene chloride was added thereto, followed by being washed four times with 70 ml of deionized water and concentrating the methylene chloride layer to 14.2 g. To this, 20 ml of diisopropyl ether was added and crystallized to yield crystals, which were filtered off and dried to yield the compound A-5 as a yellow crystal. Yield: 9.13 g (yield: 91.6%), purity: 97.2% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm). The measurement results of $^1$H-NMR by a deuterated dimethyl sulfoxide solvent are listed in Table 1-1.

Example 8

Production of Compound I-5

In a 100 ml two-neck flask, 8.31 g (0.0250 mol) of the compound A-5, 1.91 g (0.0275 g) of hydroxylamine hydrochloride, and 33.00 g of dimethylformamide were put, stirred, and dissolved. Into this, 2.29 g (0.0275 mol) of 48 mass % aqueous sodium hydroxide solution was loaded at 25° C. and stirred at 40° C. for 3 hours. To the reaction liquid, 33 ml of deionized water and 1.04 g (0.0100 mol) of 35 mass % hydrochloric acid were loaded while cooling them to be at not more than 30° C. and stirred for 30 minutes. The precipitated crystals were filtered off and dried to yield the compound I-5 as a yellow crystal. Yield: 8.29 g (yield: 95.5%). Purity: 99.9% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm). The measurement results of $^1$H-NMR by a deuterated chloroform solvent are listed in Table 1-1.

Example 9

Production of Compound S-32

In a 100 ml four-neck flask, 5.56 g (0.0160 mol) of the compound I-5, 40.00 g of ethylene dichloride, and 2.02 g (0.0200 mol) of triethylamine were put and stirred, followed by replacing the atmosphere in the system with nitrogen gas. Dropwise added was 9.23 g (0.0176 mol) of a solution of 48 mass % d-camphor sulfonyl chloride in ethylene dichloride at 15-18° C., and its temperature was increased to room temperature. After 1 hour, 25 ml of deionized water was loaded in the reaction liquid at 20° C. or less, and the ethylene dichloride layer was washed twice with 30 ml of 0.5 mass % aqueous sodium hydroxide solution, once with 30 ml of 5 mass % aqueous hydrochloric acid solution, and six times with 40 ml of deionized water, followed by being concentrated to yield a crude product. It was subjected to purification by silica gel chromatogram (developing solvent with a hexane-to-ethyl acetate volume ratio of 1 (hexane):1-2 (ethyl acetate)) to yield the compound S-32 which was a target as a yellow solid. Yield: 3.24 g (yield: 36.1%), purity: 97.4% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm). The measurement results of $^1$H-NMR by a deuterated chloroform solvent and the measurement results of MALDI TOF-MS (m/z) are listed in Table 1-1. The measurement results of MALDI TOF-MS (m/z) were 584.4 (sodium ion adduct) and 600.4 (potassium ion adduct).

Example 10

Production of Compound A-6

In a 3 L four-neck flask, 124.80 g (0.455 mol) of 4-(2-hydroxyethylthio)naphthalic anhydride (the intermediate of the compound A-5 of Example 7), 570 g of tetrahydrofuran, 550 g of dimethyl sulfoxide, 40.51 g (0.75 mol) of sodium methoxide, and 130.50 g (0.853 mol) of bromoethyl ethyl ether were put and stirred, followed by replacing the atmosphere in the system with nitrogen gas and stirring them at 50° C. for 3 hours. Added were 80 g of deionized water and 77 g of 48 mass % aqueous sodium hydroxide solution at room temperature, they were stirred at 50° C. for 3 hours, 183 g of 35 mass % hydrochloric acid was further added at room temperature, and the resultant was stirred at 50° C. for 2 hours. To the reaction liquid, 600 ml of deionized water was added and cooled to 5° C. to be crystallized to yield crystals, which were filtered off and dried to yield a crude crystal. Yield: 68.20 g. This crude crystal was subjected to purification by silica gel chromatogram (developing solvent with a hexane-to-ethyl acetate volume ratio of 1 (hexane):1 (ethyl acetate)) to yield the compound A-6 as a yellow solid. Yield: 32.40 g (yield: 20.6%), purity: 83.1% by HPLC (column: Inertsil ODS-2 manufactured by GL Sciences Inc., 4.6 mm×250 mm, solvent: acetonitrile/water=5/5, L-7455 diode array detector manufactured by Hitachi, Ltd., detection wavelength: 230 nm). The measurement results of $^1$H-NMR by a deuterated dimethyl sulfoxide solvent are listed in Table 1-2.

Example 11

Production of Compound I-6

In a 300 ml two-neck flask, 31.80 g (0.0918 mol) of the compound A-6, 7.66 g (0.110 g) of hydroxylamine hydrochloride, and 127 g of dimethylformamide were put and stirred, and the atmosphere in system was replaced with nitrogen gas. Into this, 9.17 g (0.0110 mol) of 48 mass % aqueous sodium hydroxide solution was loaded at 29-40° C. and stirred at 40° C. for 1 hour. To the reaction liquid, 127 ml of deionized water and 3.83 g (0.0367 mol) of 35 mass % hydrochloric acid were loaded while cooling them to be at not more than 30° C. and stirred for 1 hour. The precipitated crystals were filtered off and dried to yield the compound I-6 as a yellow crystal. Yield: 31.30 g (yield: 94.3%). Purity: 98.2% by HPLC (column: Inertsil ODS-2 manufactured by GL Sciences Inc., 4.6 mm×250 mm, solvent: acetonitrile/water=5/5, L-7455 diode array detector manufactured by Hitachi, Ltd., detection wavelength: 230 nm). The measurement results of $^1$H-NMR by a deuterated dimethyl sulfoxide solvent are listed in Table 1-2.

Example 12

Production of Compound S-33

In a 100 ml four-neck flask, 9.04 g (0.025 mol) of the compound I-6, 50 g of ethylene dichloride, and 3.16 g of triethylamine (0.0313 mol) were put and stirred, followed by replacing the atmosphere in the system with nitrogen gas. Dropwise added was 14.43 g (0.0275 mol) of a solution of 48 mass % d-camphor sulfonyl chloride in ethylene dichloride at 20-22° C., and its temperature was increased to room temperature. After 1 hour, 35 ml of deionized water was loaded in the reaction liquid at 20° C. or less, 60 ml of ethyl acetate was further loaded, and the organic layer was washed twice with 35 ml of 0.5 mass % aqueous sodium hydroxide solution, once with 35 ml of 3 mass % aqueous hydrochloric acid solution, and six times with 40 ml of deionized water, followed by being concentrated to yield a crude product. It was subjected to purification by silica gel chromatogram (developing solvent with a hexane-to-ethyl acetate volume ratio of 1 (hexane):1 (ethyl acetate)) to yield the compound S-33 which was a target as a yellow solid. Yield: 8.12 g (yield: 56.4%), purity: 99.3% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm). The measurement results of $^1$H-NMR by a deuterated acetone solvent are listed in Table 1-2. The measurement results of MALDI TOF-MS (m/z) were 584.4 (sodium ion adduct) and 600.4 (potassium ion adduct).

Example 13

Production of Compound S-38

In 20.00 g of ethylene dichloride, 2.81 g (0.0050 mol) of the compound S-32 was dissolved, and 20 ml of 10 mass % hydrochloric acid was added and stirred at room temperature for 24 hours. The reaction liquid was subjected to oil-water separation to yield the ethylene dichloride layer, which was washed five times with 20 ml of deionized water, followed by being concentrated and adding 20 ml of ethyl acetate to crystallize crystals, which were filtered off and dried to yield the compound S-38 which was a target. Yield: 1.26 g (yield:

50.0%), purity: 99.2% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm). The measurement results of $^1$H-NMR by a deuterated chloroform solvent are listed in Table 1-2. The measurement results of MALDI TOF-MS (m/z) were 526.4 (sodium ion adduct) and 542.3 (potassium ion adduct).

Example 14

Production of Compound S-39

In a 100 ml four-neck flask, 6.43 g (0.0180 mol) of the compound I-2, 26 g of ethylene dichloride, and 1.57 g of pyridine (0.0198 mol) were put, stirred, and dissolved, followed by replacing the atmosphere in the system with nitrogen gas. Dropwise added was 5.33 g of trifluoromethanesulfonic anhydride (0.0189 mol) at 15-20° C., and the resultant was stirred at 20° C. for 3 hours. In the reaction liquid, 18 g of deionized water and 15 g of ethylene dichloride were put, stirred, and subjected to oil-water separation to yield the ethylene dichloride layer, which was washed twice with 50 ml of 0.25 mass % aqueous sodium hydroxide solution, once with 50 ml of 5 mass % aqueous hydrochloric acid solution, and five times with 50 ml of deionized water. The solvent was distilled off from the ethylene dichloride layer, and the resultant was concentrated to 16.5 g, added with 30 g of n-heptane, and stirred. The precipitated crystals were filtered off and dried to yield the compound S-39 which was a target. Yield: 7.47 g (yield: 84.8%), purity: 98.8% by HPLC (column: CAPCELL PAK C8 DD manufactured by Shiseido Company, Limited, 4.6 mm×250 mm, solvent: acetonitrile/water=8/2, L-7455 diode array detector manufactured by Hitachi, Ltd., detection wavelength: 230 nm). The measurement results of $^1$H-NMR and $^{19}$F-NMR by a deuterated dimethyl sulfoxide solvent are listed in Table 1-3. The measurement results of MALDI TOF-MS (m/z) were 455.3 (sodium ion adduct) and 494.3 (potassium ion adduct).

Example 15

Production of Compound A-7

In a 100 ml four-neck flask, 8.567 g (0.0400 mol) of 3-hydroxynaphthalic anhydride, 48.0 g of dimethyl sulfoxide, and 10.081 g (0.0730 mol) of potassium carbonate were put and stirred, and the atmosphere in the system was replaced with nitrogen gas. Dropwise added was 11.233 g (0.0734 mol) of bromoethyl ethyl ether, and the resultant was stirred at 70° C. for 5 hours. In the reaction liquid, 12 ml of deionized water and 9.6 ml of 48% by weight aqueous sodium hydroxide solution were put, stirred at 50° C. for 2 hours, and thereafter ice-cooled, and 21.0 g of 35% by weight aqueous hydrochloric acid solution was put and stirred at 60° C. for 2 hours. The reaction liquid, 500 ml of methylene chloride, and 200 ml of deionized water were added and subjected to oil-water separation to yield the organic layer, which was washed three times with 200 ml of deionized water and thereafter concentrated, and the organic layer was concentrated and subjected to purification by silica gel chromatogram (developing solvent with a hexane-to-ethyl acetate volume ratio of 2 (hexane):3 (ethyl acetate)) to yield the compound A-7 which was a target as a pale yellow solid. Yield: 5.20 g (yield: 45.4%), purity: 98.3% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm). The measurement results of $^1$H-NMR by a deuterated dimethyl sulfoxide solvent are listed in Table 1-3.

Example 16

Production of Compound I-7

In a 100 ml four-neck flask, 4.87 g (0.0170 mol) of the compound A-7, 30.0 g of dimethylformamide, and 1.420 g (0.0204 mol) of hydroxylamine hydrochloride were put and stirred, and the atmosphere in the system was replaced with nitrogen gas. Dropwise added was 1.700 g (0.0204 mol) of 48% by weight aqueous sodium hydroxide solution at 28-30° C., and the resultant was stirred for 2 hours. Loaded were 20 ml of deionized water and 0.70 g (0.0068 mol) of 35% by weight aqueous hydrochloric acid solution while cooling them to be at not more than 30° C., and the resultant was stirred for 1 hour. The precipitated crystals were filtered off and dried to yield the compound I-7 as a pale yellow crystal. Yield: 4.62 g (yield: 90.2%). Purity: 99.6% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm). The measurement results of $^1$H-NMR by a deuterated dimethyl sulfoxide solvent are listed in Table 1-3.

Example 17

Production of Compound S-45

In a 50 ml four-neck flask, 4.520 g (0.0150 mol) of the compound I-7, 25.0 g of ethylene dichloride, and 1.310 g (0.0165 mol) of pyridine were put and stirred, and the atmosphere in the system was replaced with nitrogen. Dropwise added was 5.280 g (0.0187 mol) of trifluoromethanesulfonic anhydride at 10-15° C., and the resultant was stirred at room temperature for 5 hours. The reaction liquid, 30 ml of methylene chloride, and 30 ml of deionized water were added and subjected to oil-water separation to yield the organic layer, which was washed twice with 30 ml of 0.2% by weight aqueous sodium hydroxide solution and five times with 30 ml of deionized water, followed by being concentrated and filtering off and drying the precipitate to yield the compound S-45 which was a target as a pale yellow crystal. Yield: 3.87 g (yield: 59.5%), purity: 96.8% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm). The measurement results of $^1$H-NMR by a deuterated dimethyl sulfoxide solvent are listed in Table 1-3. The measurement results of MALDI TOF-MS (m/z) were 456.1 (sodium ion adduct) and 472.1 (potassium ion adduct).

Example 18

Production of Compound S-47

In a 100 ml four-neck flask, 11.11 g (0.0307 mol) of the compound I-6, 53 g of ethylene dichloride, and 2.67 g (0.0338 mol) of pyridine were put, stirred, and dissolved, followed by replacing the atmosphere in the system with nitrogen gas. Dropwise added was 10.38 g (0.0368 mol) of trifluoromethanesulfonic anhydride at 15-20° C., and the resultant was stirred at 20° C. for 2 hours. In the reaction liquid, 50 ml of deionized water and 50 ml of methylene chloride were put, stirred, and subjected to oil-water separation to yield the organic layer, which was washed twice with 50 ml of 0.5 mass % aqueous sodium hydroxide solution, once with 50 ml of 1 mass % aqueous hydrochloric acid solution, and five times with 50 ml of deionized water, followed by being concentrated to yield a crude product. It was subjected to purification by silica gel chromatogram (developing solvent with a hexane-to-ethyl acetate volume ratio of 3 (hexane):2 (ethyl acetate)) to yield the compound S-47 which was a target as a yellow solid. Yield: 9.26 g (yield: 61.1%), purity: 97.1% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength: 230 nm). The measurement results of $^{1}$H-NMR and $^{19}$F-NMR by a deuterated acetone solvent are listed in Table 1-3. The measurement results of MALDI TOF-MS (m/z) were 516.2 (sodium ion adduct) and 532.2 (potassium ion adduct).

Example 19

Production of Compound S-61

In a 100 ml four-neck flask, 9.76 g (0.0270 mol) of the compound I-6, 40.0 g of dimethylformamide, and 3.01 g (0.0297 mol) of triethylamine were put and stirred, and the atmosphere in the system was replaced with nitrogen gas. Gradually loaded was 2.66 g (0.0297 mol) of p-toluenesulfonate chloride at 20-26° C., and the resultant was stirred at 40° C. for 2 hours. To the reaction liquid, 80 ml of ethyl acetate and 50 ml of deionized water were added, 80 ml of methylene chloride was further put, and the resultant was stirred and subjected to oil-water separation to yield the organic layer, which was washed twice with 50 ml of 0.5 mass % aqueous sodium hydroxide solution, once with 50 ml of 3 mass % aqueous hydrochloric acid solution, and five times with 50 ml of deionized water, followed by being concentrated and filtering off and drying the precipitated crystals to yield the yellow crystal of S-61 which was a target. Yield: 6.52 g (yield: 46.8%), purity: 95.7% by HPLC (column: Inertsil ODS-2 manufactured by GL Sciences Inc., 4.6 mm×250 mm, solvent: acetonitrile/water=7/3, L-7455 diode array detector manufactured by Hitachi, Ltd., detection wavelength; 230 nm). The measurement results of $^{1}$H-NMR by a deuterated chloroform solvent are listed in Table 1-3. The measurement results of MALDI TOF-MS (m/z) were 538.3 (sodium ion adduct) and 554.3 (potassium ion adduct).

TABLE 1-1

| Compound | Measurement results ($^{1}$H-NMR) |
|---|---|
| Compound A-1 | 8.57-8.5 (m, 2H), 8.35 (d, 1H), 7.88 (t, 1H), 7.74 (d, 1H), 3.28 (d, 2H), 1.74 (tt, 2H), 1.52 (qt, 2H), 0.95 (t, 3H) |
| Compound I-1 | 10.65 (s, 1H), 8.52 (m, 2H), 8.36 (d, 1H), 7.86 (t, 1H), 7.73 (d, 1H), 3.25 (t, 2H), 1.72 (tt, 2H), 1.50 (qt, 2H), 0.94 (t, 3H) |
| Compound S-28 | 8.66 (d, 1H), 8.58 (d, 1H), 8.49 (d, 1H), 7.75 (t, 1H), 7.52 (d, 1H), 4.23 (m, 1H), 3.93 (d, 1H), 3.17 (t, 2H), 2.54-2.41 (m, 2H), 2.17-1.97 (m, 3H), 1.89-1.77 (m, 3H), 1.61-1.45 (m, 3H), 1.20 (s, 3H), 1.02-0.98 (m, 6H) |
| Compound A-2 | 8.65 (d, 1H), 8.58 (d, 1H), 8.42 (d, 1H), 7.93 (t, 1H), 7.81 (d, 1H), 3.33 (t, 2H), 1.84 (tt, 2H), 1.56 (tt, 2H), 1.40-1.29 (m, 8H), 0.87 (t, 3H) |
| Compound I-2 | 9.68 (s, 1H), 8.62-8.57 (m, 2H), 8.42 (d, 1H), 7.89 (t, 1H), 7.77 (d, 1H), 3.29 (t, 2H), 1.83 (tt, 2H), 1.55 (tt, 2H), 1.40-1.28 (m, 8H), 0.88 (t, 3H) |
| Compound S-29 | 8.60-8.54 (m, 2H), 8.41 (d, 1H), 7.86 (t, 1H), 7.71 (d, 1H), 4.16 (d, 1H), 4.02 (d, 1H), 3.27 (t, 2H), 2.44-2.40 (m, 2H), 2.19-1.95 (m, 3H), 1.86-1.74 (m, 3H), 1.60-1.52 (m, 3H), 1.40-1.23 (m, 8H), 1.18 (s, 3H), 0.97 (s, 3H), 0.87 (t, 3H) |

TABLE 1-1-continued

| Compound | Measurement results ($^{1}$H-NMR) |
|---|---|
| Compound A-5 | 8.63 (d, 1H), 8.54 (d, 1H), 8.38 (d, 1H), 7.92 (t, 1H), 7.84 (d, 1H), 4.66 (s, 2H), 3.83 (t, 2H), 3.56-3.50 (m, 4H), 1.09 (t, 3H) |
| Compound I-5 | 8.64-8.59 (m, 2H), 8.45 (d, 1H), 7.75 (t, 1H), 7.60 (d, 1H), 4.74 (s, 2H), 3.93 (t, 2H), 3.64 (q, 2H), 3.43 (t, 2H), 1.22 (t, 3H) |
| Compound S-32 | 8.68-8.64 (m, 2H), 8.52 (d, 1H), 7.79 (t, 1H), 7.64 (d, 1H), 4.73 (s, 2H), 4.24 (d, 1H), 3.94-3.91 (m, 3H), 3.64 (q, 2H), 3.43 (t, 2H), 2.50-2.40 (m, 2H), 2.17-1.97 (m, 3H), 1.89-1.82 (m, 1H), 1.51-1.46 (m, 1H), 1.28-1.20 (m, 6H), 0.98 (s, 3H) |

TABLE 1-2

| Compound | Measurement results ($^{1}$H-NMR) |
|---|---|
| Compound A-6 | 8.58-8.52 (m, 2H), 8.34 (d, 1H), 7.91 (t, 1H), 7.79 (d, 1H), 3.79 (t, 2H), 3.59 (t, 2H), 3.50-3.40 (m, 6H), 1.09 (t, 3H) |
| Compound I-6 | 10.66 (s, 1H), 8.57-8.52 (m, 2H), 8.37 (d, 1H), 7.88 (t, 1H), 7.82 (d, 1H), 3.77 (t, 2H), 3.57 (t, 2H), 3.48-3.45 (m, 4H), 3.41 (q, 2H), 1.07 (t, 3H) |
| Compound S-33 | 8.71 (d, 1H), 8.66 (d, 1H), 8.50 (d, 1H), 7.97 (t, 1H), 7.93 (d, 1H), 4.17 (d, 1H), 4.05 (d, 1H), 3.89 (t, 2H), 3.64 (t, 2H), 3.55-3.52 (m, 4H), 3.45 (t, 2H), 2.47-2.40 (m, 2H), 2.21-2.11 (m, 2H), 1.97 (s, 1H), 1.79-1.74 (m, 1H), 1.57-1.51 (m, 1H), 1.20 (s, 3H), 1.11 (t, 3H), 0.98 (s, 3H) |
| Compound S-38 | 8.66-8.63 (m, 2H), 8.49 (d, 1H), 7.77 (t, 1H), 7.64 (d, 1H), 4.23 (d, 1H), 4.01 (q, 2H), 3.92 (d, 1H), 3.42 (t, 2H), 2.54-2.42 (m, 2H), 2.17-1.97 (m, 4H), 1.89-1.83 (m, 1H), 1.51-1.48 (m, 1H), 1.20 (s, 3H), 0.98 (s, 3H) |

TABLE 1-3

| Compound | Measurement results (upper: $^{1}$H-NMR, lower: $^{19}$F-NMR) |
|---|---|
| Compound S-39 | 8.69-8.64 (m, 2H), 8.47 (d, 1H), 7.96 (t, 1H), 7.82 (d, 1H), 3.30 (t, 2H), 1.74 (tt, 2H), 1.47 (tt, 2H), 1.36-1.23 (m, 8H), 0.85 (t, 3H)<br>−69.36 |
| Compound A-7 | 8.38-8.32 (m, 2H), 8.06 (s, 1H), 8.02 (s, 1H), 7.84 (t, 1H), 4.35 (t, 2H), 3.80 (t, 2H), 3.56 (q, 2H), 1.16 (t, 3H) |
| Compound I-7 | 10.7 (s, 1H), 8.31-8.27 (m, 2H), 8.02 (s, 1H), 7.90 (s, 1H), 7.79 (t, 1H), 4.33 (t, 2H), 3.80 (t, 2H), 3.57 (q, 2H), 1.16 (t, 3H) |
| Compound S-45 | 8.45-8.43 (m, 2H), 8.18 (s, 1H), 8.09 (s, 1H), 7.89 (t, 1H), 4.38 (t, 2H), 3.81 (t, 2H), 3.56 (q, 2H), 1.15 (t, 3H) |
| Compound S-47 | 8.73-8.67 (m, 2H), 8.51 (d, 1H), 7.99-7.91 (m, 2H), 3.92 (t, 2H), 3.65 (t, 2H), 3.56-3.52 (m, 4H), 3.46 (q, 2H), 1.11 (t, 3H)<br>−68.69 |
| Compound S-61 | 8.63-8.61 (m, 2H), 8.47 (d, 1H), 8.03 (d, 2H), 7.76 (t, 1H), 7.63 (d, 1H), 7.42 (d, 2H), 3.86 (t, 2H), 3.67 (t, 2H), 3.60 (t, 2H), 3.52 (q, 2H), 3.41 (t, 2H), 2.50 (s, 3H), 1.22 (t, 3H) |

Evaluation Example 1

Measurement of UV Absorption Spectra

Solutions of the compounds listed in Table 2 among the compounds yielded in the above described examples and the comparative compounds 1-3 represented by the formulae described below in methanol with $1 \times 10^{-5}$ mol/liter were prepared to measure the UV absorption spectra of the solutions at 200 nm to 500 nm. The maximum values of the absorption peaks of the respective compounds and their absorbances are listed in Table 2.

TABLE 2

| | Maximum absorption (nm) Absorbance | Maximum absorption (nm) Absorbance |
| --- | --- | --- |
| Compound S-29 | 210 0.299 | 400 0.158 |
| Compound S-32 | 203 0.726 | 396 0.167 |
| Compound S-33 | 209 0.343 | 400 0.141 |
| Compound S-38 | 206 1.514 | 396 0.156 |
| Compound S-39 | 210 0.386 | 400 0.143 |
| Compound S-45 | 230 0.397 | 377 0.024 |
| Compound S-47 | 212 0.370 | 395 0.113 |
| Compound S-61 | 204 0.452 | 394 0.160 |
| Comparative compound 1 | 231 0.413 | 335 0.133 |
| Comparative compound 2 | 226 0.389 | 336 0.103 |
| Comparative compound 3 | 229 0.513 | 335 0.117 |

Comparative compound 1

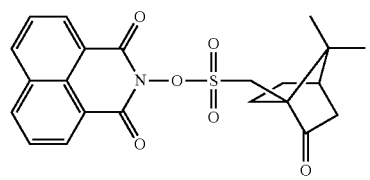

Comparative compound 2

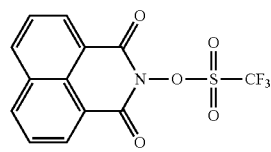

Comparative compound 3

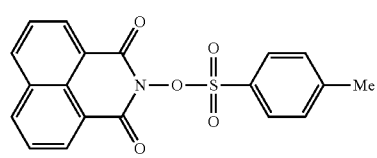

Table 2 described above exhibits that all of the sulfonic acid derivative compounds according to the present invention have absorptions indicating the maximum values at around 400 nm. In contrast, the comparative compounds 1-3 do not have any absorption in this range but have absorptions indicating the maximum values at 340 nm. This exhibits that the sulfonic acid derivative compound according to the present invention is advantageous from the viewpoint of having photosensitivity even for light sources with long wavelengths like g-ray and h-ray. That is, the sulfonic acid derivative compound according to the present invention is useful as a photoacid generator and a cationic polymerization initiator.

Evaluation Example 2

Evaluation of Solubility

The solubilities of the compounds yielded in the above described examples and listed in Table 3 and the comparative compounds 1-3 represented by the above described formula in various organic solvents at 25° C. were evaluated by concentration (mass %). The results are listed in Table 3. The concentrations in the table are those at which undissolution did not occur and stable solutions were exhibited. The case in which dissolution occurred at more than 20 mass % is indicated by 20<while the case of less than 0.5 mass % is indicated by 0.5>.

TABLE 3

| Compound | Propylene glycol monomethyl ether acetate | Cyclohexanone | γ-Butyrolactone |
| --- | --- | --- | --- |
| Compound S-28 | 2.8 | 14.0 | 17.8 |
| Compound S-29 | 9.0 | 20< | 20< |
| Compound S-32 | 20< | 20< | 20< |
| Compound S-33 | 13.2 | 20< | 20< |
| Compound S-39 | 5.2 | 20< | 3.0 |
| Compound S-47 | 20< | 20< | 20< |
| Compound S-61 | 1.2 | 9.0 | 12.2 |
| Comparative compound 1 | 1.1 | 6.1 | 12.6 |
| Comparative compound 2 | 1.9 | 7.1 | 4.8 |
| Comparative compound 3 | 0.5> | 1.0 | 1.9 |

It can be confirmed from Table 3 described above that the sulfonic acid derivative compounds according to the present invention exhibit good solubilities in the various organic solvents. In contrast, the comparative compounds 1-3 had low solubilities in all the organic solvents. This exhibits that the sulfonic acid derivative compound according to the present invention may be used at high concentration in a photosensitive composition such as a photoresist composition or a cationically polymerizable composition and can improve the sensitivity of the photosensitive composition. This also exhibits that the preservation stability of the photosensitive composition can be improved since a satisfactory dissolution margin can be ensured. Furthermore, it is exhibited that it contributes to improvement in developability when it is used in a photoresist composition using an organic developing solution.

Evaluation Example 3

Evaluation of Resist Sensitivity

The resist abilities of the compounds listed in Table 4 and yielded in the above described examples and a comparative compound 2 were evaluated. In a 50 ml brown screw pipe, 5.00 g of a polymer (number average molecular weight of 4400, mass-average molecular mass of 12000) of a copolymer (mole fraction of 4:4:2) of tetrahydro-2-oxofuran-3-yl-methacrylate, 2-methyl-2-adamanthylmethacrylate, and 3-hydroxy-1-adamanthylmethacrylate, 15.00 g of methyl ethyl ketone, and 0.025 g of BYK-307 were put, stirred, and dissolved. In a 6 ml brown screw pipe, 4.00 g of the polymer solution and 0.04 g of the above described respective compounds were put, stirred, and dissolved to prepare resist liquids. The resist liquids were coated on aluminum plates by a bar coater #3, respectively, dried at 80° C. for 10 minutes, and thereafter exposed to light using a high-pressure mercury lamp and an irradiation spectroscope. They were baked at 140° C. for 2 minutes, developed by immersing them in a 2.38% by weight aqueous tetramethylammonium hydroxide solution for 30 seconds, and sufficiently washed with deionized water. Light exposure values necessary for curing were calculated from patterns formed by irradiation with light with wavelengths of 365, 405, and 436 nm. The results are listed in Table 4.

TABLE 4

|  | Light exposure sensitivity [J/cm²] | | |
| --- | --- | --- | --- |
|  | 365 nm | 405 nm | 435 nm |
| Comparative compound 2 | 1.0 | >33 | >33 |
| Compound S-39 | 0.33 | 0.59 | 1.9 |
| Compound S-45 | 0.10 | 0.59 | >33 |
| Compound S-47 | 0.19 | 0.33 | 1.0 |

It was confirmed from the results of Table 4 that the resist compositions employing the naphthalimide sulfonic acid ester compounds according to the present invention had high resist sensitivity and were especially advantageous as positive resist compositions in comparison with those employing the comparative compound.

The invention claimed is:

1. A sulfonic acid derivative compound represented by the formula (I)

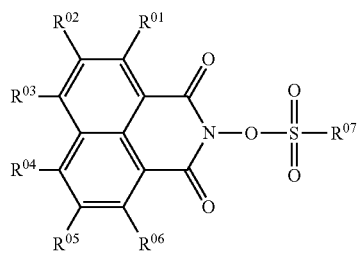

(wherein $R^{01}$, $R^{04}$, $R^{05}$, and $R^{06}$ represent a hydrogen atom; any one of $R^{02}$ and $R^{03}$ represents an alkoxy group having a carbon number of 4 to 18 which may be substituted with an alicyclic hydrocarbon group, a heterocyclic group, or a halogen atom and which may have a branch; a group in which a methylene group which is not adjacent to an oxygen atom in the alkoxy group but is at an optional position is substituted with —C(=O)— group; a group in which the alkoxy group is interrupted by a —O—C(=O)— bond or a —OC(=O)—NH— bond from closer proximity to a naphthalene ring; an alkylthio group having a carbon number of 4 to 18 which may be substituted with an alicyclic hydrocarbon group, a heterocyclic group, or a halogen atom and which may have a branch; a group in which a methylene group which is not adjacent to a sulfur atom in the alkylthio group but is at an optional position is substituted with a —C(=O)— group; a group in which the alkylthio group is interrupted by a —O—C(=O)— bond or a —OC(=O)—NH— bond from closer proximity to a naphthalene ring; or a group represented by the formula (A) as described below; the remaining one of $R^{02}$ and $R^{03}$ represents a hydrogen atom; and $R^{07}$ represents an aliphatic hydrocarbon group having a carbon number of 1 to 18 which may be substituted with a halogen atom and/or an alkylthio group; an alkyl group having a carbon number of 1 to 18 which may be substituted with a halogen atom and/or an alicyclic hydrocarbon group and which may have a branch; an alicyclic hydrocarbon group having a carbon number of 3 to 18 which may be substituted with a halogen atom; an aryl group having a carbon number of 6 to 20 which may be substituted with a halogen atom and/or an alkylthio group having a carbon number of 1 to 18; an arylalkyl group having a carbon number of 7 to 20 which may be substituted with a halogen atom and/or an alkylthio group having a carbon number of 1 to 18; an alkylaryl group having a carbon number of 7 to 20 which may be substituted with a halogen atom; an aryl group having a carbon number of 7 to 20 which is substituted with an acyl group; 10-camphoryl; or a group represented by the formula (B) as described below)

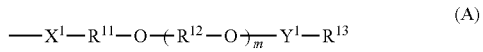

(wherein $X^1$ represents an oxygen atom or a sulfur atom; $Y^1$ represents a single bond or an alkanediyl group having a carbon number of 1 to 4; $R^{11}$ represents a hydrocarbon group having a carbon number of 1 to 12; $R^{12}$ represents an alkanediyl group having a carbon number of 1 to 4; $R^{13}$ represents a hydrogen atom, an alkyl group having a carbon number of 1 to 4 which may have a branch, or an alicyclic hydrocarbon group or a heterocyclic group having a carbon number of 3 to 10; m represents 0 to 5; and plural $R^{12}$ may be the same or different when m is 2 to 5)

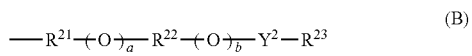

(wherein $Y^2$ represents a single bond or an alkanediyl group having a carbon number of 1 to 4; $R^{21}$ represents an alkanediyl group having a carbon number of 2 to 6, a halogenated alkanediyl group having a carbon number of 2 to 6, an arylene group having a carbon number of 6 to 20, or a halogenated arylene group having a carbon number of 6 to 20; $R^{22}$ represents a single bond, an alkanediyl group having a carbon number of 2 to 6, a halogenated alkanediyl group having a carbon number of 2 to 6, an arylene group having a carbon number of 6 to 20, or a halogenated arylene group having a carbon number of 6 to 20; $R^{23}$ represents an alkyl group having a carbon number of 1 to 18 which may have a branch, a halogenated alkyl group having a carbon number of 1 to 18 which may have a branch, an alicyclic hydrocarbon group having a carbon number of 3 to 12, an aryl group having a carbon number of 6 to 20, a halogenated aryl group having a carbon number of 6 to 20, an arylalkyl group having a carbon number of 7 to 20, or a halogenated arylalkyl group having a carbon number of 7 to 20; a and b represent 0 or 1; and either a or b is 1).

2. The sulfonic acid derivative compound according to claim 1, wherein the $R^{07}$ is a perfluoroalkyl group having a carbon number of 1 to 8.

3. The sulfonic acid derivative compound according to claim 1, wherein the $R^{07}$ is 10-camphoryl.

4. The sulfonic acid derivative compound according to claim 1, wherein any one of the $R^{02}$ and $R^{03}$ is a group represented by the formula (A).

5. A compound represented by the formula (III) as described below

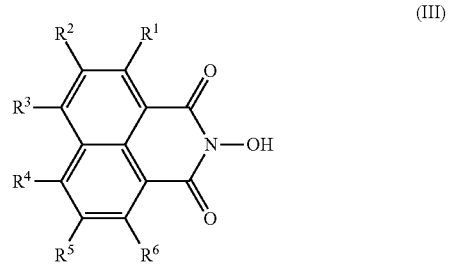

(wherein $R^1$, $R^4$, $R^5$, and $R^6$ represent a hydrogen atom; any one of $R^2$ and $R^3$ represents an alkylthio group having a carbon number of 4 to 18 which may be substituted with an alicyclic hydrocarbon group, a heterocyclic group, or a halogen atom and which may have a branch; a group in which a methylene group which is not adjacent to a sulfur atom in the alkylthio group but is at an optional position is substituted with a —C(=O)— group; a group in which the alkylthio group is substituted with a —O—C(=O)— bond or a —OC(=O)—NH— bond from closer proximity to a naphthalene ring; or a group represented by the formula (D) as described below; and the remaining one of $R^2$ and $R^3$ represents a hydrogen atom)

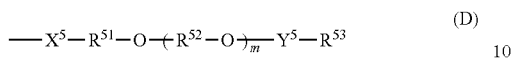 (D)

(wherein $X^5$ represents an oxygen atom or a sulfur atom; $Y^5$ represents a single bond or an alkanediyl group having a carbon number of 1 to 4; $R^{51}$ represents a hydrocarbon group having a carbon number of 1 to 12; $R^{52}$ represents an alkanediyl group having a carbon number of 1 to 4; $R^{53}$ represents an alkyl group having a carbon number of 1 to 4 which may have a branch or a hydrocarbon group or a heterocyclic group having a carbon number of 3 to 10; m represents 0 to 5; and plural $R^{52}$ may be the same or different when m is 2 to 5).

6. The sulfonic acid derivative compound according to claim 2, wherein any one of the $R^{02}$ and $R^{03}$ is a group represented by the formula (A).

7. The sulfonic acid derivative compound according to claim 3, wherein any one of the $R^{02}$ and $R^{03}$ is a group represented by the formula (A).

* * * * *